(12) United States Patent
Holm et al.

(10) Patent No.: US 8,546,637 B2
(45) Date of Patent: Oct. 1, 2013

(54) MEDICAL ARTICLES AND METHODS OF MAKING USING IMMISCIBLE MATERIAL

(75) Inventors: David R. Holm, Hudson, WI (US); Dong-Wei Zhu, Shoreview, MN (US)

(73) Assignee: 3M Innovative Properties Company, Saint Paul, MN (US)

( * ) Notice: Subject to any disclaimer, the term of this patent is extended or adjusted under 35 U.S.C. 154(b) by 241 days.

(21) Appl. No.: 12/942,489

(22) Filed: Nov. 9, 2010

(65) Prior Publication Data
US 2011/0112457 A1  May 12, 2011

Related U.S. Application Data

(60) Provisional application No. 61/259,622, filed on Nov. 9, 2009, provisional application No. 61/301,386, filed on Feb. 4, 2010.

(51) Int. Cl.
*A61F 13/00*  (2006.01)
(52) U.S. Cl.
USPC ............................................. 602/42; 602/52
(58) Field of Classification Search
USPC ............................ 602/42–54; 428/343, 354
See application file for complete search history.

(56) References Cited

U.S. PATENT DOCUMENTS

| | | |
|---|---|---|
| 2,736,721 A | 2/1956 | Dexter |
| RE24,906 E | 12/1960 | Ulrich |
| 4,310,509 A | 1/1982 | Berglund |
| 4,323,557 A | 4/1982 | Rosso |
| 4,472,480 A | 9/1984 | Olson |
| 4,499,896 A | 2/1985 | Heinecke |
| 4,595,001 A | 6/1986 | Potter |
| 4,737,410 A | 4/1988 | Kantner |
| 4,747,401 A | 5/1988 | Potter |
| 4,798,201 A | 1/1989 | Rawlings |
| 4,833,179 A | 5/1989 | Young |
| 4,871,812 A | 10/1989 | Lucast |
| 5,120,781 A | 6/1992 | Johnson, Jr. |
| 5,209,971 A | 5/1993 | Babu |
| 5,214,119 A | 5/1993 | Leir |
| 5,531,855 A | 7/1996 | Heinecke |
| 5,622,711 A | 4/1997 | Chen |
| 5,633,010 A | 5/1997 | Chen |
| 5,641,506 A | 6/1997 | Talke |
| 5,738,642 A | 4/1998 | Heinecke |
| 5,849,325 A | 12/1998 | Heinecke |
| 5,908,693 A | 6/1999 | Delgado |
| 6,083,856 A | 7/2000 | Joseph |

(Continued)

FOREIGN PATENT DOCUMENTS

| | | |
|---|---|---|
| EP | 1 255 575 | 11/2002 |
| WO | WO 02-066087 | 8/2002 |

(Continued)

OTHER PUBLICATIONS

ASTM Designation: E-96-80, "Standard Test Methods for Water Vapor Transmission of Materials", 1980, pp. 337-346.

(Continued)

*Primary Examiner* — Michael A. Brown
(74) *Attorney, Agent, or Firm* — Trisha D. Adamson

(57) ABSTRACT

Provided are medical articles (e.g., wound dressings) that include a pressure sensitive adhesive layer and methods of making the medical articles using immiscible materials that increase moisture vapor transmission rates.

29 Claims, 4 Drawing Sheets

(56) References Cited

U.S. PATENT DOCUMENTS

| | | |
|---|---|---|
| 6,171,985 B1 | 1/2001 | Joseph |
| 6,198,016 B1 | 3/2001 | Lucast |
| 6,262,329 B1 | 7/2001 | Brunsveld |
| 6,264,976 B1 | 7/2001 | Heinecke |
| 6,441,082 B1 | 8/2002 | Weitzel |
| 6,495,229 B1 | 12/2002 | Carte |
| 6,518,343 B1 | 2/2003 | Lucast |
| 6,518,359 B1 | 2/2003 | Clemens |
| 6,548,727 B1 | 4/2003 | Swenson |
| 6,558,790 B1 * | 5/2003 | Holguin et al. ........... 428/355 R |
| 6,642,304 B1 | 11/2003 | Hansen |
| 6,838,589 B2 * | 1/2005 | Liedtke et al. .................. 602/58 |
| 6,903,151 B2 | 6/2005 | Lucast |
| 7,160,976 B2 | 1/2007 | Lühmann |
| 7,612,248 B2 | 11/2009 | Burton |
| 7,745,509 B2 | 6/2010 | Burton |
| 7,858,838 B2 | 12/2010 | Holm |
| 2003/0054025 A1 | 3/2003 | Cantor |
| 2004/0133143 A1 | 7/2004 | Burton |
| 2006/0159732 A1 | 7/2006 | Cullen |
| 2006/0246296 A1 | 11/2006 | Xia |
| 2008/0107718 A1 | 5/2008 | Baron |
| 2008/0115889 A1 | 5/2008 | Hall |
| 2009/0186221 A1 * | 7/2009 | Yatagai et al. .......... 428/355 AC |
| 2011/0112458 A1 | 5/2011 | Holm et al. |

FOREIGN PATENT DOCUMENTS

| | | |
|---|---|---|
| WO | WO 2008-074333 | 6/2008 |
| WO | WO 2009-006901 | 1/2009 |
| WO | WO 2009-086840 | 7/2009 |
| WO | WO 2009-088648 | 7/2009 |
| WO | WO 2011-057175 | 5/2011 |

OTHER PUBLICATIONS

ASTM Designation: D3330/D3330M-04 (Reapproved 2010), "Standard Test Methods for Peel Adhesion of Pressure-Sensitive Tape1", 2004, pp. 1-6.

"Glossary of Terms—Pressure Sensitive Tape Council", Pressure Sensitive Tape Council, Naperville, Illinois, USA [on line], [last access date from the internet on Apr. 9, 2012], URL <http://www.pstc.org/i4a/pages/index.cfm?pageid=3336>, 5 pages.

SATAS, Handbook of Pressure Sensitive Adhesive Technology, 172-173 (1989).

Xu,"Microporous Polypropylene Hollow fiber membranes Part II", Journal of Membrane Science, Mar. 2003, vol. 214, No. 1, pp. 71-81.

International Search Report for PCT/US2010/55958, mailed Jan. 7, 2011, 5 pages.

International Search Report for PCT/US2010/55778, mailed Jan. 7, 2011, 6 pages.

* cited by examiner

MEDICAL ARTICLES AND METHODS OF MAKING USING IMMISCIBLE MATERIAL

CROSS REFERENCE TO RELATED APPLICATION

This application claims the benefit of U.S. Provisional Patent Application No. 61/259,622, filed Nov. 9, 2009 and U.S. Provisional Patent Application No. 61/301,386, filed Feb. 4, 2010, the disclosures of which are incorporated by reference herein in their entirety.

BACKGROUND OF THE INVENTION

This disclosure relates to medical articles, and more particularly to wound dressings and medical tapes for use on skin and wounds. Wound dressings and tapes may need to adhere to a variety of skin types and remain effective in the presence of various amounts of moisture, whether a low exuding wound, a high exuding wound, or a patient that is diaphoretic. In all of these circumstances, the wound dressing or tape is desirably able to respond to dynamic levels of moisture present to ensure adequate wear time. Modifications to medical articles to improve permeability to moisture are known and include, for example, selectively or pattern coating an adhesive onto a permeable film surface or creating new adhesives with higher moisture permeability. Examples of selective adhesive coating may include a continuous polymeric thin film having a pressure sensitive adhesive (PSA) that is selectively coated on one surface of the polymeric thin film such that 40 to 75 percent of the film surface does not contain adhesive. Moisture is preferably transmitted through the areas without adhesive.

While the pattern or selective coating may result in medical articles with higher moisture transmission rates, pattern coated adhesive in certain situations can have poor edge adhesion, resulting in edge lift. The methods and equipment used to pattern coat an adhesive can be more expensive and elaborate than the methods and equipment used for coating the adhesive in a continuous film-type manner. In addition, the methods and equipment can be quite specialized for a particular adhesive system and not interchangeable between different adhesive systems.

Methods of creating different adhesive properties are also known, and include adding additives to PSA copolymers. Plasticizers, humectants, inorganic salts, organic salts, or microcolloids may be added to a pressure sensitive adhesive to enhance breathability and make the adhesive suitable for medical articles. Such compounds are fully mixed in and/or dispersed throughout the adhesive prior to construction of a medical article. Thus, the adhesive composition as a whole is made more permeable to moisture by uniform dispersion or mixing of hydrophilic materials. In many cases these uniformly mixed or dispersed additives can significantly change the properties of the adhesive properties throughout the adhesive, especially in the presence of high moisture conditions.

SUMMARY OF THE INVENTION

The present application provides for targeted modification of adhesive systems to improve moisture vapor transmission rate (MVTR) by providing an MVTR-modifying material that is not uniformly dispersed in the bulk of the adhesive layer. In preferred embodiments, the MVTR-modifying material is only minimally dispersed, or not dispersed at all, in the bulk of the adhesive layer. Embodiments of the present invention provide high MVTR medical articles that can be obtained for a wide variety of PSAs instead of or in addition to pattern coating of the adhesive or formulating an inherently high MVTR adhesive system that can also stick adequately to skin under a variety of conditions.

In some embodiments, pressure sensitive adhesives of the present invention advantageously retain consistent adhesive properties prior to contact with fluid in combination with an MVTR-modifying material. Embodiments of the present invention allow for modification of permeability and adhesion in discrete, controlled locations in an adhesive layer. As the entire adhesive layer need not be modified, portions of the adhesive layer on the side in contact with a target site, e.g., skin, may retain consistent and desirable adhesion properties regardless of moisture or humidity levels that the adhesive is exposed to during storage or use.

In one embodiment, the present invention provides a medical article (e.g., a wound dressing, medical tape, surgical drape, etc.) that includes: a PSA layer including acidic-functional groups or basic-functional groups, wherein the PSA includes at least 0.84 mmoles acidic- or basic-functional groups per gram PSA; and an MVTR-modifying material that is basic when the PSA includes acidic-functional groups or is acidic when the PSA includes basic-functional groups; wherein the MVTR-modifying material is immiscible with the PSA, and reacts with the functional groups upon contact to form a poly-salt in the presence of fluid.

In some embodiments, the adhesive contains greater than 0.42 mmoles of acidic- or basic-functional groups per gram of PSA that can be neutralized by the MVTR-modifying material. More preferably, the adhesive contains at least 0.69 mmoles of these functional groups per gram of PSA. Even more preferably, the adhesive contains 0.84 mmoles of these functional groups. Even more preferably, the adhesive contains at least 1.3 mmoles of these functional groups. Even more preferably, the adhesive contains at least 1.80 mmoles of these functional groups. Even more preferably, the adhesive contains at least 2.08 mmoles of these functional groups. In most embodiments, the adhesive contains between 1.3 mmoles and 2.5 mmoles of these functional groups.

Preferably, the adhesive should contain no greater than 5.6 mmoles of these functional groups per gram of PSA. More preferably, the adhesive contains no greater than 4.2 mmoles of these functional groups per gram of PSA, and even more preferably no greater than 2.8 mmoles of these functional groups per gram of PSA.

In certain embodiments, the PSA comprises a functional polymer, and the polymer is prepared from at least 6 wt-% acidic- or basic-functional monomers, based on the total weight of the PSA. In certain embodiments, the functional polymer is a (meth)acrylate (i.e., (meth)acrylic) polymer.

In certain embodiments, medical articles of the present invention include an amount of MVTR-modifying material relative to functionalized groups in the PSA such that the molar ratio of the MVTR-modifying material to the acid/base functional groups is within a range of 0.1:1 to 100:1 per volume of adhesive under the surface area treated with the MVTR-modifying material.

Various constructions of the medical articles are provided. In one embodiment, the MVTR-modifying material is disposed on a surface of the PSA layer. In some embodiments, the MVTR-modifying material can be pattern coated onto the surface of the PSA layer.

If desired, a second PSA layer can be included, which may be the same or different than the first PSA layer, wherein the MVTR-modifying material is disposed between the two PSA layers.

In certain embodiments, medical articles of the present invention include a scaffold. In certain embodiments, the MVTR-modifying layer includes the scaffold. In certain preferred embodiments, the MVTR-modifying material is incorporated within a scaffold that is in contact with the PSA layer. The scaffold can include a variety of substrates suitable to function as a carrier for the MVTR-modifying material. In a preferred embodiment, the scaffold is a nonwoven fabric.

In certain embodiments, medical articles of the present invention include a backing (i.e., backing layer) and the MVTR-modifying material is disposed between the PSA layer and the backing In certain embodiments the MVTR-modifying material is in contact with both the PSA layer and the backing In certain embodiments, medical articles of the present invention include a pH-altering layer, wherein the MVTR-modifying material is disposed between the PSA layer and the pH-altering layer. In certain embodiments, the pH-altering layer includes a pH-altering material selected from the group consisting of polyacrylic acid, citric acid, lactic acid, or combinations thereof. In certain embodiments, the MVTR-modifying material is in contact with both the PSA layer and the pH-altering layer.

In certain embodiments, medical articles of the present invention include a filtration layer, wherein the filtration layer is disposed between the MVTR-modifying material and a fluid source or target site (e.g., a wound).

In certain embodiments, medical articles, particularly wound dressings, of the present invention include an absorbent layer or pad, wherein the absorbent layer includes a polymeric fabric, a polymeric foam, or a combination thereof.

In certain embodiments, medical articles of the present invention include a carrier film in contact with the PSA layer; an absorbent pad disposed between the carrier film and the adhesive layer; and a backing disposed between a support layer and the PSA layer.

In certain embodiments, medical articles of the present invention include a PSA layer that includes acid-functional groups, and an MVTR-modifying material that is basic. For such PSAs, the MVTR-modifying material includes a base selected from a group consisting of sodium hydroxide, potassium hydroxide, calcium hydroxide, lithium hydroxide, silver hydroxide, zinc hydroxide, ammonium hydroxide, magnesium hydroxide, barium hydroxide, strontium hydroxide, cesium hydroxide, rubidium hydroxide, ammonium carbonate, sodium carbonate, sodium bicarbonate, potassium carbonate, potassium bicarbonate, silver carbonate, lithium carbonate, lithium bicarbonate, barium bicarbonate, magnesium carbonate, cesium carbonate, hydrates thereof, and combinations thereof. Preferably, the MVTR-modifying material is not a multi-valent cation that may cause crosslinking of the PSA polymers to the extent that such crosslinking reduces wet MVTR.

In certain embodiments, medical articles of the present invention include a PSA layer that includes basic-functional groups, and an MVTR-modifying material that is acidic. For such PSAs, the MVTR-modifying material includes, for example, an acid capable of reacting with an amine group to form a poly-salt.

In certain embodiments, the PSA includes rubber based adhesives (e.g., tackified natural rubbers, synthetic rubbers, and styrene block copolymers), (meth)acrylics (i.e., (meth) acrylates), poly(alpha-olefins), polyurethanes, and silicones. In certain embodiments, the PSA includes an amine adhesive (e.g., that includes a polymer with basic amine groups in the backbone, pendant therefrom, or both). In certain embodiments, the PSA includes a polymer having carboxylic acid groups. In certain embodiments, the acid groups, or part of the acid groups, in the PSA can be incorporated by mixing tackifiers or other additives with the above mentioned polymers.

In certain embodiments, medical articles of the present invention have a wet MVTR of at least 1200 g/m$^2$/24 hours. In certain embodiments the MVTR-modifying material improves (i.e., increases) the wet MVTR of the medical article by at least 20% relative to the same article without the MVTR-modifying material. In certain embodiments, the MVTR-modifying material improves (i.e., increases) the dry MVTR of the medical article by at least 10% relative to the same article without the MVTR-modifying material.

In certain embodiments, the PSA layer does not include MVTR-modifying material uniformly dispersed throughout.

In one embodiment, the present invention provides a wound dressing that includes:

a backing having a first major surface and a second major surface; a PSA layer disposed on at least a portion of the first major surface of the backing; wherein the PSA includes acid-functional groups or basic-functional groups, wherein the PSA includes at least 0.84 mmoles of the functional groups per gram of PSA; and an MVTR-modifying layer proximate the PSA layer; wherein the MVTR-modifying layer includes an MVTR-modifying material that is basic when the PSA includes acidic-functional groups, or is acidic when the PSA includes basic-functional groups; wherein the MVTR-modifying material is immiscible with the PSA, and reacts with the functional groups upon contact to form a poly-salt in the presence of fluid. In certain embodiments, the MVTR-modifying layer is in direct contact with at least a portion of the PSA layer. In certain embodiments, one or more layers are disposed between the MVTR-modifying layer and the PSA layer.

In one embodiment, the present invention provides a wound dressing that includes: a backing having a first major surface and a second major surface; a PSA layer disposed on at least a portion of the first major surface of the backing; wherein the PSA includes acid-functional groups; a support layer releasably adhered to the second major surface of the backing; and an MVTR-modifying layer including MVTR-modifying material in contact with the PSA layer, wherein the PSA layer does not include MVTR-modifying material uniformly dispersed throughout; wherein the MVTR-modifying material is basic, is immiscible with the PSA, and reacts with the functional groups upon contact to form a poly-salt in the presence of fluid. Preferably, the PSA includes at least 0.84 mmoles of the functional groups per gram of PSA.

In one embodiment, the present invention provides a wound dressing that includes: a backing having a first major surface and a second major surface; a PSA layer disposed on at least a portion of the first major surface of the backing; wherein the PSA includes a (meth)acrylate polymer having acid-functional groups, wherein the polymer is prepared from at least 6 wt-% acidic-functional monomers, based on the total weight of the PSA; a support layer releasably adhered to the second major surface of the backing; and an MVTR-modifying layer including an MVTR-modifying material in contact with the PSA layer; wherein the MVTR-modifying material is basic, is immiscible with the PSA, and reacts with the functional groups upon contact to form a poly-salt in the presence of fluid.

The present invention also provides methods of increasing the MVTR of an adhesive layer in a medical article. In one embodiment, the method includes: providing a PSA layer including acid-functional groups or basic-functional groups, wherein the PSA includes at least 0.84 mmoles of the functional groups per gram of PSA; providing an MVTR-modifying material that is basic when the PSA includes acidic-functional groups or is acidic when the PSA includes basic-functional groups, wherein the MVTR-modifying material is immiscible with the PSA; and placing the MVTR-modifying material in the medical article at a location that allows the MVTR-modifying material to contact the PSA when the medical article comes in contact with fluid during use (e.g., when applied to the skin or wound of a subject); wherein contact between the MVTR-modifying material, the PSA, and fluid causes an acid-base reaction to form a poly-salt and increase the moisture permeability of at least a portion of the PSA layer.

In one embodiment, the method includes: providing a PSA layer including a polymer having acid-functional groups or a polymer having basic-functional groups, wherein the polymer is prepared from at least 6 wt-% total acidic- or basic-functional monomers, based on the total weight of the PSA; providing an MVTR-modifying material that is basic when the PSA includes an acidic-functional group or is acidic when the PSA includes a basic-functional group, wherein the MVTR-modifying material is immiscible with the PSA; and placing the MVTR-modifying material in the medical article at a location that allows the MVTR-modifying material to contact the PSA when the medical article comes in contact with fluid during use; wherein contact between the MVTR-modifying material, the PSA, and fluid causes an acid-base reaction to form a poly-salt and increase the moisture permeability of at least a portion of the PSA layer.

In certain embodiments of the methods, placing the MVTR-modifying material in the medical article at a location that allows the MVTR-modifying material to contact the PSA includes coating (e.g., pattern coating) the MVTR-modifying material onto the PSA layer.

In certain embodiments of the methods, placing the MVTR-modifying material in the medical article at a location that allows the MVTR-modifying material to contact the PSA includes: providing a scaffold; coating the scaffold with the MVTR-modifying material; and contacting at least a portion of the PSA layer with the coated scaffold. This could be done in addition to directly coating the MVTR-modifying material onto the PSA layer.

The ability to modify MVTR, instead of (or in addition to) pattern coating an adhesive on a permeable film or mixing hydrophilic additives to the adhesive in bulk, makes the present invention particularly well suited for medical articles such as medical tapes, bandages, feminine hygiene pads, diapers, surgical drapes, and various wound dressings. A practitioner or manufacturer may effectively control the level of moisture permeability for a given portion of an adhesive layer, allowing for narrow tailoring to the nature and requirements of the patient's malady. Instead of a compromise between adhesion and permeability, the present invention allows for optimization of both of these characteristics.

Herein, "fluid" means water, water vapor, serum, wound exudate, sweat, and other liquid or vapor compositions.

Herein, "layer" means a single stratum that may be continuous or discontinuous over a surface.

Herein, "absorbent" means that the material is preferably capable of absorbing fluids, particularly body fluids.

Herein, "poly-salt" means a polymer having at least one ionic group.

Herein, "immiscible" or "incompatible" means that a material is not capable of penetrating into the core of a 0.25 centimeter (cm) cross-section of an adhesive layer. To examine immiscibility, a small portion of an adhesive polymer may be cut into a 0.25 cm thick×2.5 cm wide×10 cm long strip. The polymer is then placed in contact with the MVTR-modifying material for 24 hours at 25 degrees Celsius and 20% to 50% relative humidity. A cross-section of the adhesive strip is then analyzed for presence of MVTR-modifying material at the center of the section. An incompatible or immiscible MVTR-modifying material will only slightly penetrate the adhesive polymer, if at all, but not into the core (i.e., center) of a 0.25-cm cross-section of an adhesive layer.

Herein, "medical article" means wound dressings, surgical drapes, tapes, bandages, diapers, feminine hygiene products, and combinations thereof. Preferred medical articles include tapes, wound dressings, and bandages.

Herein, "PSA comprising an acidic-functional group," "polymer comprising an acidic-functional group," "PSA comprising acidic functional groups" or "polymer comprising acidic-functional groups" means that the PSA, or polymer included therein, has an excess of acidic groups (e.g., carboxylic acid groups) if there are both acidic and basic groups present, such that the PSA, or polymer included therein, is acidic.

Herein, "PSA comprising a basic-functional group," "polymer comprising a basic-functional group," "PSA comprising basic functional groups" or "polymer comprising basic-functional groups" means that the PSA, or polymer included therein, has an excess of basic groups, if there are both acidic and basic groups present, such that the PSA, or polymer included therein, is basic.

The terms "comprises" and variations thereof do not have a limiting meaning where these terms appear in the description and claims.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, "a," "an," "the," "at least one," and "one or more" are used interchangeably. Thus, for example, an adhesive polymer that comprises "an" acid functional group can be interpreted to mean that the adhesive polymer includes "one or more" acid functional groups. Similarly, a medical article comprising "a" filtration layer can be interpreted to mean that the article includes "one or more" filtration layers.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE DRAWINGS

The invention will be further described with reference to the drawings, wherein corresponding reference characters indicate corresponding parts throughout the several views, and wherein.

Figure 1:
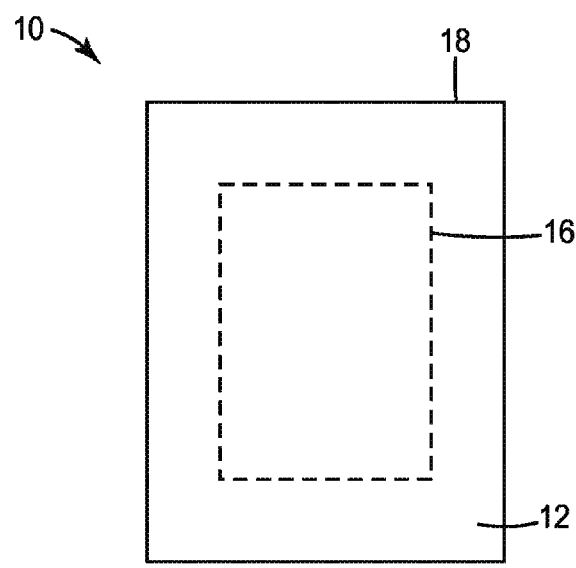
FIG. 1 is a top view of a wound dressing according to one embodiment of the present invention.

The MVTR-modifying material may be depicted in the Figures as confined to discrete portions of the wound dressing. This is not, however, intended to limit the location or relative concentration of the MVTR-modifying material unless specifically noted. Layers in the depicted embodiments are for illustrative purposes only and are not intended to define the relative thickness or position of any component.

DETAILED DESCRIPTION OF ILLUSTRATIVE EMBODIMENTS

The present invention is directed to a medical article having a PSA layer and methods of making medical articles more permeable to moisture. Through the use of different MVTR-modifying materials and different concentrations of MVTR-modifying materials, the PSA layer may be modified to meet desired adhesion properties and moisture vapor transmission properties. For example, modified wound dressings of the present invention may have a relatively low dry MVTR and a relatively high wet MVTR that vary in locations within the dressing and adhesion properties that vary within the dressing. These MVTR properties allow the wound under the dressing to heal in moist conditions without causing the skin surrounding the wound to become macerated, and to facilitate optimum wear time and ease of removal.

In some embodiments of the invention, an MVTR-modifying layer includes the MVTR-modifying material that interacts with the acid or base functional groups in a PSA layer. For example, if the PSA includes functional groups that are basic, the MVTR-modifying material will be acidic. Similarly, if the PSA includes functional groups that are acidic, the MVTR-modifying material will be basic. The MVTR-modifying material may be placed on or near a surface of the PSA layer. Although not wishing to be bound by theory, when the medical article is placed on a patient at a target site, fluid may cause the MVTR-modifying material to interact with the acid/base groups of the polymer, resulting in an increase to the MVTR of the PSA layer.

Herein, dry MVTR (or upright MVTR) of the PSA layer, or the medical article, is measured by ASTM E-96-80 (American Society of Testing Materials) at 38° C. and 20% relative humidity using an upright cup method. Wet MVTR (or inverted MVTR) is measured by the same method except that the sample jars are inverted so the water is in direct contact with the test sample.

Factors influencing the MVTR include, but are not limited to, the thickness of the PSA layer, the amount of hydrophilic ingredients in the PSA, concentration of acid/base functionality within the PSA layer and the amount of MVTR-modifying material, the composition and structure of the backing film, the coating structure (i.e., continuous, fibrous, film, or pattern) of the adhesive, and the overall construction of a medical article (e.g., number and arrangement of various layers, films, etc.).

When compared to the dry MVTR of an untreated medical article of identical composition and construction with a continuous layer of adhesive, the dry MVTR of the medical article that has been treated with MVTR-modifying composition according to the present invention is preferably greater than the untreated medical article by a factor of at least 1.2 (at least 20%) more, preferably at least 3, even more preferably at least 5, and even more preferably at least 10.

When compared to the wet MVTR of an untreated medical article of identical composition and construction, the wet MVTR of the medical article that has been treated with an MVTR-modifying material according to the present invention is preferably greater than the untreated medical article by a factor of at least 1.2 (at least 20%) more, preferably at least 3, even more preferably at least 5, and even more preferably at least 10. The medical article that has been treated preferably has a wet MVTR of at least 1200 g/m$^2$/24 hours, more preferably at least 3000 g/m$^2$/24 hours, even more preferably at least 7500 g/m$^2$/24 hours, and even more preferably at least 15000 g/m$^2$/24 hours. Different regions of the medical article may include different MVTR values.

The PSA layer is modified by the MVTR-modifying material due to interfacial interactions as a result of an acid-base interaction between the two materials. This acid-base interaction is a Lewis acid-base type interaction. Lewis acid-base interactions require that one chemical component be an electron acceptor (acid) and the other an electron donor (base). The electron donor provides an unshared pair of electrons and the electron acceptor furnishes an orbital system that can accommodate the additional unshared pair of electrons. The following general equation describes the Lewis acid-base interaction:

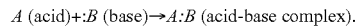

$A$ (acid)$+$:$B$ (base)$\rightarrow A$:$B$ (acid-base complex).

The MVTR-modifying material is immiscible in or incompatible with the PSA layer when the article is not in contact with fluid, such as water or moisture. Accordingly, the MVTR-modifying material will not react appreciably with the adhesive until fluid is present. When the MVTR-modifying material does interact with the adhesive layer in the presence of fluid, a Lewis acid-base reaction occurs and portions of the adhesive in contact with the MVTR-modifying material are neutralized. This neutralization and creation of ionic bonds increases the polarity of discrete portions of the adhesive layer, which results in increased MVTR. In essence, this allows for the possibility of the modification of the MVTR "on demand" (e.g., when applied dry to the target site and contacted with fluid). Alternatively, fluid (e.g., water) could be added to the medical article prior to packaging.

The modification of the PSA by the MVTR-modifying material is independent of the particular functionality of the respective PSA and the MVTR-modifying material. That is, either the PSA or the MVTR-modifying material can contain the acid or the base functionality. For example, an acid functionalized polymer in the adhesive layer can be paired with a basic MVTR-modifying material. Alternatively, a base functionalized polymer of the adhesive layer can be paired with an acidic MVTR-modifying material.

In one embodiment of the invention, the MVTR-modifying material comprises an inorganic base. Suitable examples of inorganic bases are sodium hydroxide, potassium hydroxide, calcium hydroxide, lithium hydroxide, silver hydroxide, zinc hydroxide, ammonium hydroxide, magnesium hydroxide, barium hydroxide, strontium hydroxide, cesium hydroxide, rubidium hydroxide, sodium carbonate, ammonium carbonate, sodium bicarbonate, potassium carbonate, potassium bicarbonate, silver carbonate, lithium carbonate, lithium bicarbonate, barium bicarbonate, magnesium carbonate, cesium carbonate, the hydrates of these inorganic bases, or combinations thereof. In preferred embodiments, the MVTR-modifying material is sodium carbonate, sodium bicarbonate, potassium carbonate, potassium bicarbonate, or hydrates thereof. Various combinations can be use if desired. Preferably, the MVTR-modifying material is not a multi-valent cation that may cause crosslinking of the PSA polymers to the extent that such crosslinking reduces wet MVTR.

In another embodiment of the invention, the MVTR-modifying material is an organic base. Suitable organic bases include, but are not limited to poly(ethyleneimine), poly(ethyloxazoline), and other polymers containing amino functional groups such as poly(N,N-dimethylaminoethyl acrylate). Suitable organic bases should be incompatible with or immiscible in the PSA.

In some embodiments, the MVTR-modifying material includes acidic functionality. Acidic MVTR-modifying material may be inorganic or organic acids. Suitable examples of inorganic acids include, but are not limited to, sulfuric acid, hydrochloric acid, nitric acid, phosphoric acid, and mixtures thereof. Organic acids may be used, but should be limited to compounds not miscible/compatible with the PSA having basic functionality, such as formic acid. Preferably, the organic acid is monofunctional.

In addition to the MVTR-modifying material, an MVTR-modifying layer may further include other materials incompatible/immiscible with the PSA that may also help improve MVTR or other properties, but do not appreciably react with the acid- or base-functional groups in the PSA. Suitable materials, for example, include sodium chloride and potassium chloride.

Polymers suitable for PSAs in the present invention are those containing acidic or basic functionalities which on neutralization yield ionic functionalities. Additionally or alternatively, the acid groups, or part of the acid groups, in the PSA can be incorporated by mixing acid-functional tackifiers or other acid-functional additives with the polymers of the PSA. Such groups, whether as part of the PSA polymer or other additives, may be the same or different. Similarly, the basic groups, or part of the basic groups, in the PSA can be incorporated by mixing tackifiers or other additives with the polymers of the PSA. Such groups, whether as part of the PSA polymer or other additives, may be the same or different.

As used in the present invention, an "acidic-functional polymer" is a polymer that includes acidic-functional groups, which can be, for example, derived from at least one acidic monomer and at least one non-acidic copolymerizable monomer (i.e., a monomer that can not be titrated with a base). Alternatively, polymers can be chemically modified to include acidic functional groups. The acidic polymer may optionally include other copolymerizable monomers, such as vinyl monomers and basic monomers, as long as the resultant polymer can still be titrated with a base. Thus, usually more acidic monomers are utilized to prepare the acidic polymers than basic monomers. The acid-functional groups in any one polymer may be the same or different.

A "basic-functional polymer" is a polymer that includes basic-functional groups, which can be, for example, derived from at least one basic monomer and at least one nonbasic copolymerizable monomer (i.e., a monomer that cannot be titrated with an acid). Alternatively, polymers can be chemically modified to include basic functional groups. Other monomers can be copolymerized with the basic monomers (e.g., acidic monomers, vinyl monomers, and (meth)acrylate monomers), as long as the basic copolymer retains its basicity (i.e., it can still be titrated with an acid). Also, a basic-functional polymer can be an amine-containing polymer, wherein the amine groups are in the backbone, pendant therefrom, or both. The basic-functional groups in any one polymer may be the same or different.

For a given treatment area, defined as the volume of PSA confined within the surface area of an MVTR-modifying layer proximate to or in contact with a pressure sensitive adhesive layer, the level of MVTR-modifying material needed to increase the MVTR through the adhesive is based on the relative molar amounts of base/acid functional groups of the MVTR-modifying material to the acid/base functional groups of the adhesive that are available for neutralization for a given treatment area. Preferably, the molar ratio of MVTR-modifying material to total acid/base functional groups in the adhesive per given volume treated (i.e., the volume under the surface area treated) should range from 0.1:1 to 100:1. More preferably, this ratio is 0.2:1 to 50:1, and even more preferably 0.4:1 to 25:1.

In some embodiments, the adhesive contains greater than 0.42 mmoles of acidic- or basic-functional groups per gram of PSA that can be neutralized by the MVTR-modifying material. More preferably, the adhesive contains at least 0.69 mmoles of these functional groups per gram of PSA. Even more preferably, the adhesive contains 0.84 mmoles of these functional groups. Even more preferably, the adhesive contains at least 1.3 mmoles of these functional groups. Even more preferably, the adhesive contains at least 1.80 mmoles of these functional groups. Even more preferably, the adhesive contains at least 2.08 mmoles of these functional groups. In most embodiments, the adhesive contains between 1.3 mmoles and 2.5 mmoles of these functional groups.

Preferably, the adhesive should contain no greater than 5.6 mmoles of these functional groups per gram of PSA. More preferably, the adhesive contains no greater than 4.2 mmoles of these functional groups per gram of PSA, and even more preferably no greater than 2.8 mmoles of these functional groups per gram of PSA.

In some embodiments of the present invention, MVTR-modifying material is in direct contact with the PSA layer. The MVTR-modifying material can be directly disposed on the surface or may alternatively be incorporated into a scaffold, in both circumstances creating an MVTR-modifying layer in contact with a surface of the PSA layer. The MVTR-modifying layer may extend continuously across a portion of the PSA layer or may be disposed in discrete locations. In additional embodiments of the present invention, a filtration layer can be disposed between the target site and the MVTR-modifying layer or alternatively between the PSA layer and the MVTR-modifying layer. In other embodiments of the invention, a pH-altering layer is disposed between the target site and the MVTR-modifying layer to modify pH. In some embodiments, the medical article of the present invention may include a backing layer (i.e., backing) In another embodiment, the MVTR-modifying layer can be disposed between a first and second PSA layer.

The methods described herein involve use of an aqueous (i.e., water) solution to dispose the MVTR-modifying material on a substrate (e.g., the PSA layer, the scaffold, etc). It is also envisioned that other solvents known to those having skill in the art can be utilized. As can also be appreciated by those having skill in the art, the methods can utilize a neat MVTR-modifying composition (i.e., without a solvent).

Figure 2A:
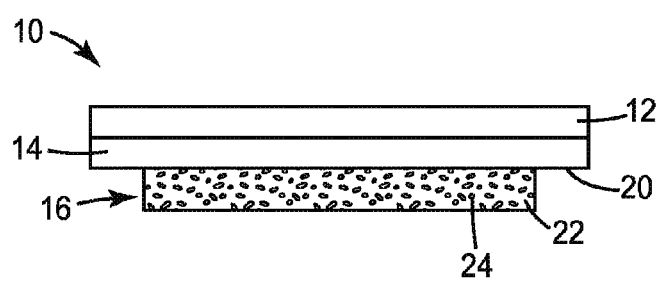
FIG. 2a is a side view of the wound dressing of FIG. 1.

Starting with reference to FIGS. 1 and 2*a*, a wound dressing according to one embodiment of the disclosure is depicted. FIG. 1 is a top view of the wound dressing, and FIG. 2 is a side view of the wound dressing of FIG. 1. Wound dressing 10 includes a backing layer 12, a PSA layer 14 on one surface of the backing layer 12, and an MVTR-modifying layer 16 attached to a portion of the PSA layer 14. The MVTR-modifying layer 16 does not fully extend to the periphery 18 of the PSA layer 14, so that portions of the exposed surface 20 of the PSA layer 14 are not in contact with the MVTR-modifying layer 16. It is also contemplated that in some embodiments the MVTR-modifying layer extends to the periphery of the PSA layer, in that the MVTR-modifying layer and the PSA layer are coextensive.

According to the embodiment depicted in FIGS. 1 and 2*a*, the MVTR-modifying layer 16 is comprised of a scaffold 22 and an MVTR-modifying material 24 incorporated into or deposited on the surface of said scaffold 22. Exemplary materials useful for the scaffold are described in further detail below. As depicted in FIG. 2*a*, the MVTR-modifying layer 16 is a layer on a portion of the PSA layer 14. The MVTR-modifying layer 16 may be centrally located on the surface of the PSA layer 14, or it may be offset in any direction. Location of the MVTR-modifying layer 16 relative to the center of the dressing may be governed by the nature and location of the target site and the intended application of the modified adhesive layer 14. A given treatment area can be defined by the portions of the MVTR-modifying layer 16 in contact with or attached to the surface of the PSA layer 14. This limited contact area and relative molar concentrations of reactive groups may serve to prevent the entire PSA layer 14 from being modified by the MVTR-modifying material 24. Targeted modification in the treatment area may allow for portions of the PSA layer 14 to retain desirable adhesion to skin when in contact with fluid.

MVTR-modifying material may be impregnated in or deposited on the scaffold by any suitable method for adding the desired functionality to a substrate. FIG. 2*a* depicts the former embodiment, wherein the scaffold 22 is impregnated with MVTR-modifying material 24. In one embodiment, the scaffold is dip coated in an aqueous solution containing a concentration of the MVTR-modifying material. The scaffold is saturated and then drawn out of the aqueous solution. The scaffold is then dried. It is further contemplated that the scaffold retains some moisture when placed in contact with the PSA layer.

Figure 2B:
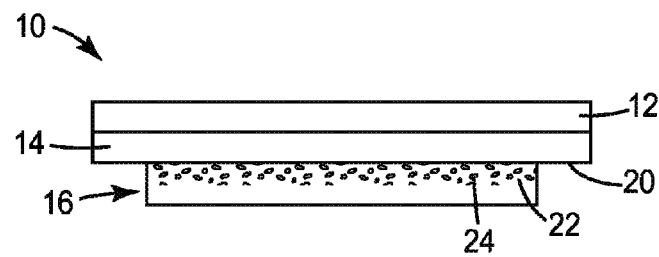
FIG. 2b is a side view of the wound dressing according to an alternative embodiment of the wound dressing of FIG. 1.

FIG. 2*b* depicts another embodiment, wherein the MVTR-modifying material 24 is deposited onto a surface of the scaffold 22. In one such embodiment, the MVTR-modifying material is nonuniformly coated on or otherwise impregnated in the scaffold 22. In one embodiment, the scaffold is dip coated in an aqueous solution containing a concentration of the MVTR-modifying composition. The scaffold is saturated and then drawn out of the aqueous solution. An aqueous solution used in the aforementioned method may further include a concentration of C1-C4 alcohol that is readily removed during drying.

The MVTR-modifying material may be placed on a surface of the scaffold or the adhesive layer in any number of patterns, including but not limited to, discrete wells, parallel rows or columns, and intersecting mesh networks. These same methods could be used to directly apply the MVTR-modifying material to the PSA layer.

In further embodiments of the invention, incorporation of the MVTR-modifying material may be achieved by coating of surfaces or impregnation of substrates with solutions, pure materials, or particle loading of webs. These coating or impregnation methods include flood coating, spray coating, pattern coating using a gravure roll, knife coating, slot die coating, inkjet printing, powder coating, or particle loading of webs.

Once scaffold 22 has been impregnated or coated with MVTR-modifying material 24 to form the MVTR-modifying layer 16, the MVTR-modifying layer 16 may be attached to the PSA layer 14 by methods known to those skilled in the arts of converting, lamination, coating, and/or needle tacking.

Alternatively or additionally, the MVTR-modifying material can be directly applied to the PSA layer and/or the backing layer. For example, the PSA can be directly laminated to or coated on a backing that is coated with the MVTR-modifying material. For an island type dressing, individual pads containing the MVTR-modifying material can be cut from a web and placed on an adhesive coated backing using rotary converting or other known converting methods. For a multi-layer product, there are a variety of methods of attaching the MVTR-modifying material to the adhesive layer such as lamination and rotary converting, and other converting methods known to those having skill in the art.

Figure 3A:
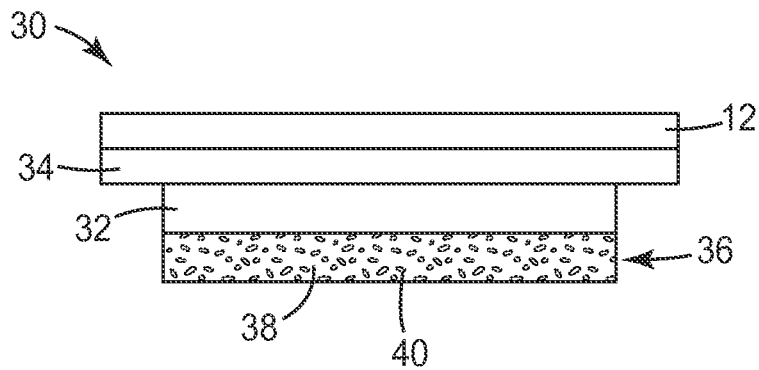
FIG. 3a is a side view of a wound dressing according to a further embodiment of the present invention.
Figure 3B:
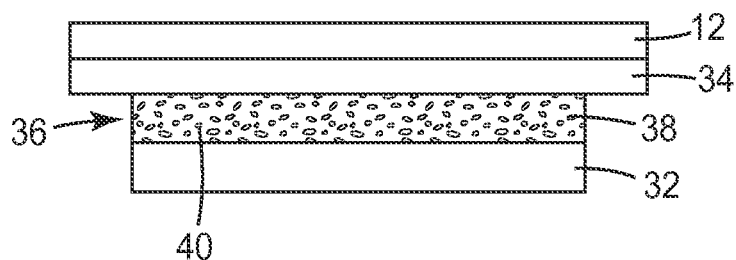
FIG. 3b is a side view of the wound dressing according to a further embodiment of the present invention.

FIGS. 3*a* and 3*b* depict additional embodiments of the invention. A wound dressing 30 may further include a filtration layer 32 in addition to an adhesive layer 34 and an MVTR-modifying layer 36. Like MVTR-modifying layer 16 of the previous embodiment, the MVTR-modifying layer 36 comprises a scaffold 38 and an MVTR-modifying material 40. The filtration layer 32 does not initially incorporate an MVTR-modifying material, although during use, the MVTR-modifying material may migrate into and through the filtration layer 32.

In the embodiment depicted in FIG. 3*a*, the filtration layer 32 is disposed between the adhesive layer 34 and the MVTR-modifying layer 36. Accordingly, the MVTR-modifying layer 36 and the bulk of the MVTR-modifying material 40 are not in contact with the adhesive layer 34 when the wound dressing is initially placed on the target site. As fluid is generated and exuded by the wound or other target site, the MVTR-modifying material 40 may migrate with the fluid through the filtration layer 32 to the adhesive layer 34. It is also contemplated that ambient moisture may carry small amounts of MVTR-modifying material 40 into the filtration layer 32 prior to use. The filtration layer 32 may be used to selectively filter molecules that might be present in the fluid generated by the wound or other target site. The aforementioned filtering may occur physically, with specifically designed porosity, for example.

FIG. 3*b* depicts an alternative embodiment of the invention, wherein a filtration layer 32 is disposed on the target site-facing side (e.g., wound-facing side) of the MVTR-modifying layer 36. In such an embodiment, the filtration layer 32 serves to reduce premature neutralization or deactivation of the MVTR-modifying material 40 before it can interact with the adhesive layer 34. The filtration layer 32 may be used to selectively filter molecules that might be present in the fluid generated by the wound or other target site. The aforementioned filtering may occur physically, with specifically designed porosity, for example. It is also contemplated that a second filtration layer may be positioned between the adhesive layer 34 and the MVTR-modifying layer 36, as is shown in FIG. 3a. The filtration layer 32 could alternatively or additionally be a pH-altering layer.

Figure 4:
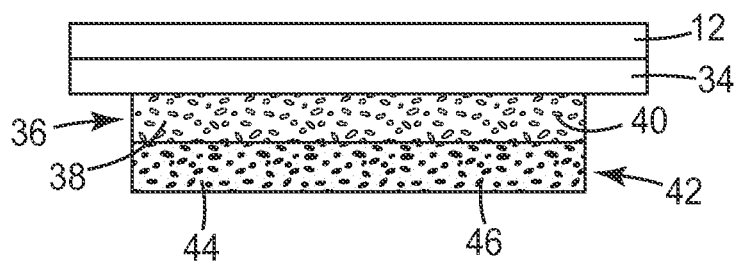
FIG. 4 is a side view of a wound dressing in a further embodiment of the present invention.

Turning to FIG. 4, another embodiment includes a pH-altering layer 42 disposed between the MVTR-modifying layer 36 and the target site. The pH-altering layer 42 includes a pH-altering material 46. In some embodiments, the pH-altering material 46 has a different pKa or pKb than the pKa or pKb of the MVTR-modifying material 40. The pH-altering material may include citric acid, polyacrylic acid, other pH-altering materials known to those having skill in the art, and combinations thereof. For example, the pH-altering layer 42 could include citric acid, and the MVTR-modifying material may be sodium carbonate. Inclusion of the pH-altering layer 42 with pH-altering material 46 to the medical article may provide buffering capabilities in order to reduce overall pH change of the fluid as it passes through the layers. Although not wishing to be bound by theory, the pH-altering layer 42 in this embodiment may also serve to prevent the MVTR-modifying material 40 from adversely modifying the pH of a target site. Although not shown in FIG. 4, the pH-altering layer 42 may extend beyond the periphery of the MVTR-modifying layer and be attached to the adhesive layer 34.

The filtration layer 32 and/or pH-altering layer 42 may include the same or similar material as scaffold 38. The filtration layer 32 and/or pH-altering layer 42 may also include a different material, though preferably one that is capable of absorbing moisture. The pH-altering material 46 may be incorporated into a second scaffold 44 or deposited on the surface thereof by using various methods as described above.

Figure 5:
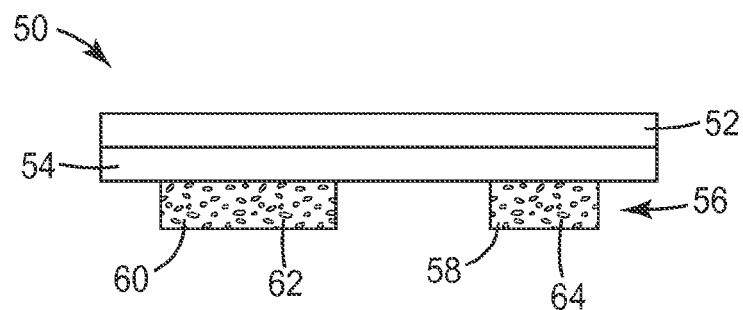
FIG. 5 is a side view of a wound dressing according to a further embodiment of the present invention.

FIG. 5 depicts a wound dressing according to one embodiment of the invention. Unlike the other embodiments heretofore depicted, wound dressing 50 includes a discontinuous MVTR-modifying layer 56. As depicted in FIG. 5, MVTR-modifying layer 56 is comprised of two or more scaffolds (58, 60) on separate portions of the adhesive layer 54. Both scaffolds (58, 60) may incorporate MVTR-modifying material (62, 64). The MVTR-modifying material 64 incorporated in the first scaffold 58 may be the same as the MVTR-modifying material 62 incorporated into the second scaffold 60, so that the MVTR of the adhesive layer 54 exposed to the MVTR-modifying material (62, 64) is essentially the same. It is also contemplated that the two MVTR-modifying materials (62, 64) may be different or present at different concentrations, such that portions of the adhesive layer 54 may have varying MVTR.

Figure 6:
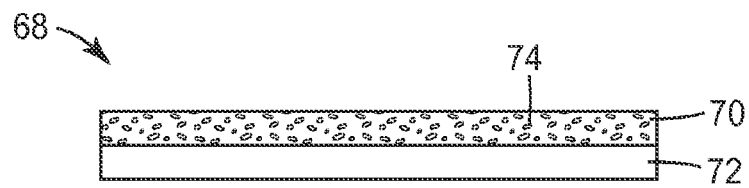
FIG. 6 is a side view of a medical tape according to an embodiment of the present invention.

The concepts of the present invention may also be utilized to create surgical tapes or similar articles. FIG. 6 depicts such an embodiment. Surgical tape 68 includes a backing layer 70 and a pressure sensitive adhesive layer 72 on one surface of the backing layer 70. MVTR-modifying material 74 is incorporated into the backing layer 70 by methods as described above.

Figure 7:
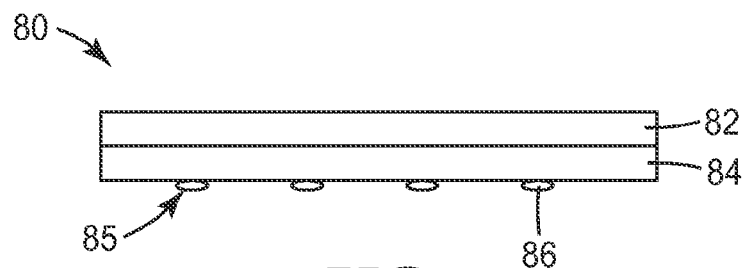
FIG. 7 is a side view of a medical tape in a further embodiment of the present invention.

In an alternative embodiment, MVTR-modifying material may be deposited, coated, or placed directly on a surface of the PSA layer. As depicted in FIG. 7, medical article 80 comprises a PSA layer 84 disposed on backing layer 82. The MVTR-modifying layer 85 includes discrete portions of MVTR-modifying material 86, but does not include a scaffold on the target site-facing surface. Alternatively or additionally, the PSA layer 84 may also include sections of MVTR-modifying material 86 on discrete portions of the surface between the PSA layer 84 and the backing layer 82. It is contemplated, though not depicted, that the embodiment further include filtration layers affixed to the target site-facing surface of the adhesive layer 84.

MVTR-modifying material 86 may be placed in contact with the adhesive layer 84 by various methods as described above, including, but not limited to, pattern, spray, and powder coating. In operation, this method of MVTR modification allows for selective and localized modification of moisture permeability and adhesion without the inclusion of a scaffold.

Figure 8:
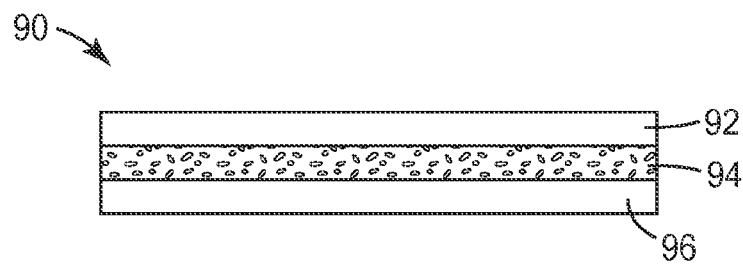
FIG. 8 is a side view of a medical article in a further embodiment of the present invention.

FIG. 8 depicts another embodiment of the disclosure, wherein an MVTR-modifying layer 94 is disposed between a backing layer 92 and a PSA layer 96. MVTR-modifying layer 94 may include a scaffold (not shown) and an MVTR-modifying material. The MVTR-modifying layer 94 may be extended along an entire surface of the adhesive layer 96. It is also contemplated (though not depicted) that the PSA layer 96 and the backing layer 92 may extend beyond the periphery of the MVTR-modifying layer 94.

The backing layer 92 may be extruded directly onto the MVTR-modifying layer 94. The MVTR-modifying layer and backing layer construction may then be laminated directly onto the PSA layer 96. Exemplary methods of extrusion and laminating may be found in for example European Patent No. 1 255 575.

Figure 9:
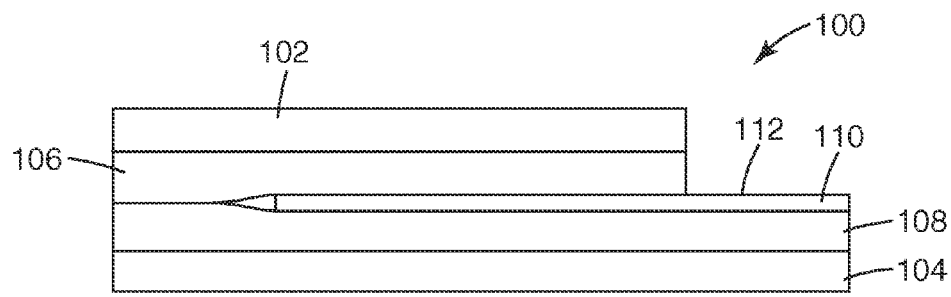
FIG. 9 is a side view of a medical article according to an embodiment of the present invention.

A further embodiment of the disclosure is depicted in FIG. 9. A wound wick 100 may include two backing layers (102, 104) operably attached to two PSA layers (106, 108). PSA layer 106 can be laminated or otherwise attached to PSA layer 108, such that the backing and PSA layers partially enclose an MVTR-modifying layer 110. Wound wick 100 features an exposed portion 112 of the MVTR-modifying layer 110.

A further embodiment of the disclosure is a kit (not shown) including an MVTR-modifying layer, a PSA layer, and a backing layer. The MVTR-modifying layer may comprise a scaffold including MVTR-modifying material. The PSA layer may be provided laminated or otherwise affixed to the backing layer. The scaffold may be provided separately from the PSA and backing Preferably no portion of the scaffold is in contact with a surface of the PSA layer prior to use. The scaffold may be placed at any desired location on the surface of the PSA layer, on the surface of the backing layer, or proximate either. The shape and/or size of the scaffold may also be modified if so desired. It is also contemplated that the MVTR-modifying material may be provided separately (i.e., without a scaffold) so that it may be deposited, coated, or placed directly on a surface of the PSA layer by the practitioner.

Other components may also be added to the previous embodiments of the present invention without exceeding the scope of the present invention. For example, an absorbent layer may be disposed between the target site and the MVTR-modifying layer. The absorbent layer may include one or more layers of padding, including, but not limited to, polymeric films, gels, alginates, and foams. Exemplary absorbent foams are described in U.S. Pat. No. 6,548,727 (Swenson). In one embodiment, the absorbent layer comprises the foam used in the foam adhesive dressing available from 3M Company, St. Paul, Minn. under the trade name TEGADERM.

In an embodiment wherein the absorbent layer includes a pad, the absorbent pad is sometimes referred to as an "island pad" because the backing layer and PSA layer extends substantially beyond at least a portion of the periphery of the absorbent pad, and typically beyond the entire periphery of the absorbent pad. For example, the diameter of the absorbent pad can be, for example, 7.5 cm, while a backing for this pad can be 12.5 cm in diameter.

The backing layer can include a transparent elastic polymeric film (e.g., urethane) having a thickness not greater than 1 mm. The backing layer construction in this embodiment should be sufficiently stiff such that it will not fold over onto itself where it is not adequately supported by a support layer (such as described further below) or the absorbent pad. Portions of the backing layer can be as thin as 0.012 mm (12 microns).

Embodiments of the present invention may further include a support layer at least partially secured to the backing layer, for example, by heat seal bonding or with the use of an adhesive. The support layer allows for easier placement of the wound dressing on the patient. Examples of suitable support layers may be found in U.S. Pat. No. 6,838,589 (Liedtke et al.) and U.S. Pat. No. 5,738,642 (Heinecke et al.), and co-pending patent application Ser. No. 11/463,853 (Holm et al.).

Figure 10:
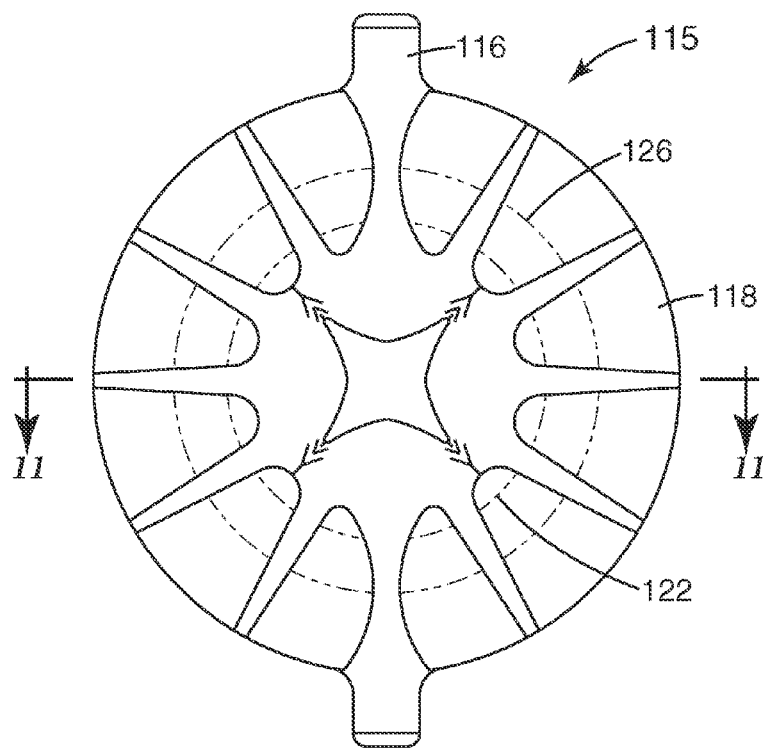
FIG. 10 is a top view of a wound dressing in a further embodiment of the present invention.

In certain implementations of the invention the support layer has a substantially radial configuration as shown in FIG. 10, with a plurality of extensions radiating generally from the center of the dressing. The support layer forms a plurality of alternating uncovered portions of the adhesive backing layer, separated from one another by the extensions along the adhesive perimeter of the wound dressing. The support layer can be a single piece of material, such as a polymeric film, or can be two or more distinct pieces.

The medical articles of the present invention can also include a facing layer. The optional facing layer includes a facing substrate and a layer of facing adhesive on the target-site facing (e.g., wound-facing) surface of the facing layer. The facing layer is liquid permeable to, e.g., allow the passage of liquid wound exudate. The facing layer can include apertures formed through the facing layer to conduct exudate from the wound surface to the other layers. The apertures may be provided as slits, voids or other openings sufficiently large to provide for the passage of liquid through the facing layer.

A facing adhesive is optionally included to assist in securing the medical article to the patient. In one embodiment, the facing adhesive is substantially coextensive with the facing layer, i.e., the facing adhesive covers substantially the entire wound-facing surface of facing layer. In such constructions, it will be understood that the apertures would preferably extend through both the facing substrate and the facing adhesive. It will be understood, however, that facing adhesive may not be provided or may be provided on only a portion of the facing substrate. For example, the facing adhesive may be coated in a strip about the periphery of the facing substrate or pattern coated on the facing substrate. It is further contemplated that the facing layer and the facing adhesive may be coextensive with the backing layer and the PSA layer, with additional components disposed there between.

The medical articles of the present invention may also include a carrier film to protect the adhesive layer until the wound dressing is ready for use. To facilitate removal, the carrier film may have a tab which overhangs the end portion of the support layer. For example, the carrier film covers the surface of the medical article applied to the patient. The carrier film remains attached to the medical article until a user is ready to apply the dressing. The carrier film may be a single piece or multiple piece release liner, and may be part of or laminated to the package (not shown) containing the dressing, or merely enclosed along with the dressing within the package. The carrier film keeps the adhesive clean during storage and shipping of the wound dressing.

Figure 11:
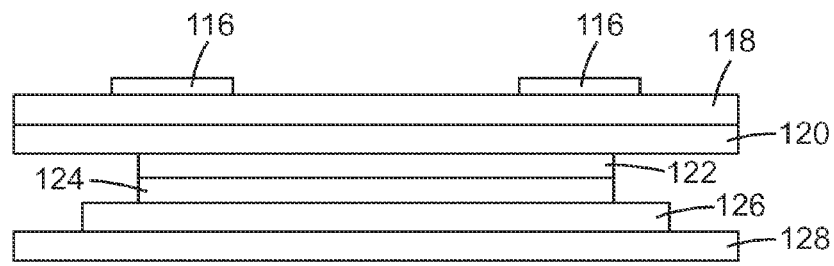
FIG. 11 is a cross-sectional view of the wound dressing of FIG. 10.

An exemplary wound dressing incorporating the carrier film, the support layer, and an absorbent layer is depicted in FIGS. 10 and 11. Wound dressing 115 includes a backing layer 118 with a first and second major surface. A PSA layer 120 is operably attached to the second major surface of the backing layer and a support layer 116 is disposed on the first major surface. An MVTR-modifying layer 122 is operably attached to a portion of the PSA layer 120. An absorbent layer including absorbent fabric 124 and absorbent foam 126 is disposed on the surface of the MVTR-modifying layer 122 opposite the PSA layer 120. As depicted, absorbent foam 126 extends beyond the periphery of the MVTR-modifying layer 122, but not to the periphery of the PSA layer 120. It is also contemplated that absorbent layer could be coextensive with the PSA layer 120. Carrier film 128 is positioned on the target site facing side of absorbent foam 126 and extends to the periphery of the adhesive layer 120. Although not shown, the carrier film may be laminated to the PSA layer 120, such that absorbent layer and MVTR-modifying layer 122 are enclosed therebetween.

It is also contemplated that wound dressings of the present invention may be provided (i.e., packaged) in at least two components. In an embodiment that consists of those elements depicted in FIGS. 10 and 11, the first component may include the support layer, backing layer, PSA layer and a carrier film. The second component may include the MVTR-modifying layer and the absorbent layer. The first and second component may be packaged or otherwise provided separately, in that no portion of the MVTR-modifying layer is in contact with the PSA layer, or proximate thereto, until the at least two components are operatively attached. Other elements, such as pH-altering layers and filtration layers may be included in the components above without departing from the scope of the invention.

As one skilled in the art would appreciate, other implementations are appropriate in order to add or take away from the aspects the various embodiments of the wound dressings as described herein. For example, the backing layer can be multiple films or materials without diverging from the invention or deviating from the meaning of the term "film" as used herein. Similarly, the absorbent pad can include multiple sub-layers, including films, webs, sheets, etc. Also, additional layers and films of other materials can be added between the materials described herein without deviating from the invention.

Additional aspects of various components that may be employed in the invention will now be described in greater detail.

Support Layer

When a support layer is used, the material used to form the support layer is generally substantially more rigid than the backing layer to prevent the backing layer from improperly wrinkling during application to a patient. The support layer can be heat-sealable to the backing layer with or without a low adhesion coating as well known in the art. In general, the support layer materials can include, but are not limited to, polyethylene/vinyl acetate copolymer-coated papers and polyester films. One example of a suitable support layer material is a polyethylene/vinyl acetate copolymer coated super calendared Kraft paper (e.g., from Loparex of Dixon, Ill.).

The support layer can include perforations to aid in separating portions of the support layer after application of the dressing in a patient. Spacing and shape of the perforations are adjusted to give a support layer with relatively easy to tear performance on removal of the support layer from the applied dressing. The perforations may be shaped in accordance with any of the accepted perforation patterns including linear, angled, Y-shaped, V-shaped, dual-angled offset, sinusoidal, etc.

Exemplary embodiments of support layer constructions that may be used in the present invention are further described in U.S. Pat. No. 5,738,642 (Heinecke et al.), and U.S. Pat. No. 6,838,589 to Liedtke et al.

Backing Layer

The backing layer, also referred to herein as a backing, typically includes a liquid impervious, moisture vapor permeable polymeric film, although it can include a variety of other materials, which are preferably used in combination with a liquid impervious, moisture vapor permeable polymeric film. The liquid impervious, moisture vapor permeable polymeric film is a conformable organic polymeric material that preferably retains its structural integrity in a moist environment. Herein, "conformable" films are those that conform to a surface, even upon movement of the surface, as with the surface of a body part. Suitable films have a composition and thickness that allow for the passage of moisture vapor through them. The film aids in the regulation of water vapor loss from the wound area beneath the dressing. The film also acts as a barrier to both bacteria and to liquid water or other liquids.

The moisture vapor permeable polymeric films for use as backing layers in the present invention can be of a wide range of thicknesses. Preferably, they are at least 10 microns (micrometers) thick, and more preferably at least 12 microns thick. Preferably, they are no greater than to 250 microns, and more preferably no greater than 75 microns thick. Furthermore, they can include one or more layers tailored to have the desired properties. These layers can be coextruded and/or bonded together with adhesive layers, for example, as long as the overall properties of the film and article, as described herein, are met.

Preferably, suitable films for use in the backing layer of the present invention have differential moisture vapor transmission properties. Preferably, a suitable film has a dry MVTR that is less than the wet MVTR of the film. Preferably, suitable films have a dry MVTR of at least 300 g/m$^2$/24 hours and a wet MVTR of at least 3000 g/m$^2$/24 hours. Preferably, the film has a wet MVTR greater than 10,000 g/m$^2$/24 hours, and more preferably greater than 15,000 g/m$^2$/24 hours. The films can be tested using the methods described above for the article.

Examples of suitable materials for the liquid-impervious, moisture-vapor permeable polymeric films of the backing layer include synthetic organic polymers including, but not limited to: polyurethanes commercially available from B.F. Goodrich, Cleveland, Ohio, under the trade designation ESTANE, including ESTANE 58237 and ESTANE 58245; polyetheramide block copolymers commercially available from Elf Atochem, Philadelphia, Pa., under the trade designation PEBAX, including PEBAX MV 1074; polyether-ester block copolymers commercially available from DuPont, Wilmington, Del., under the trade designation HYTREL. The polymeric films can be made of one or more types of monomers (e.g., copolymers) or mixtures (e.g., blends) of polymers. Preferred materials are thermoplastic polymers, e.g., polymers that soften when exposed to heat and return to their original condition when cooled. A particularly preferred material is a thermoplastic polyurethane.

Backings of the medical articles of the present invention can also include other breathable materials including, for example, nonwoven, woven, and knit webs, porous films (e.g., provided by perforations or microporous structure), foams, paper, or other known backings A preferred backing includes a combination of a liquid-impervious, moisture-vapor permeable polymeric film and a moisture-vapor permeable nonwoven web that can, among other advantages, impart enhanced structural integrity and improved aesthetics to the dressings. These layers of film and web may or may not be coextensive. A preferred such nonwoven web is a melt processed polyurethane (such as that available under the trade designation MORTHANE PS-440 from Morton International, Seabrook, N.H.), or hydroentangled nonwoven polyester or rayon-polyester webs (such as those available under the trade designation SONTARA 8010 or SONTARA 8411 from DuPont, Wilmington, Del.).

A low adhesion coating (low adhesion backsize or LAB) can be provided on the backing layer on the side that may come into contact with the support layer. The low adhesion coating reduces the need to change the dressing due to unwanted dressing removal when other tapes or devices are placed on the dressing and removed, and reduces the surface friction of the dressing on linen or other fabrics, thereby offering additional protection against the accidental removal of dressing. A description of a low adhesion backing material suitable for use with the present invention can be found in U.S. Pat. Nos. 5,531,855 and 6,264,976.

Pressure Sensitive Adhesive

Various PSAs can be used to form adhesive layer 14 on the backing layer 12 to make it adhesive. For example, PSAs may be formulated to offer good skin adhesion characteristics, offer excellent conformability, and provide a gentle release from the skin and wound site. The PSA layer can be continuous, discontinuous, pattern coated, or melt-blown, for example.

One well known means of identifying PSAs is the Dahlquist criterion. This criterion defines a PSA as an adhesive having a 1 second creep compliance of greater than $1 \times 10^{-6}$ $^{cm2}$/dyne as described in *Handbook of PSA Technology*, Donatas Satas (Ed.), 2$^{nd}$ Edition, p. 172, Van Nostrand Reinhold, New York, N.Y., 1989. Alternatively, since modulus is, to a first approximation, the inverse of creep compliance, PSAs may be defined as adhesives having a Young's modulus of less than $1 \times 10^6$ dynes/cm$^2$. Another well known means of identifying a PSA is that it is aggressively and permanently tacky at room temperature and firmly adheres to a variety of dissimilar surfaces upon mere contact without the need of more than finger or hand pressure, and which may be removed from smooth surfaces without leaving a residue as described in *Glossary of Terms Used in the Pressure Sensitive Tape Industry* provided by the Pressure Sensitive Tape Council, 1996. Another suitable definition of a suitable PSA is that it preferably has a room temperature storage modulus within the area defined by the following points as plotted on a graph of modulus versus frequency at 25° C.: a range of moduli from approximately $2 \times 10^5$ to $4 \times 10^5$ dynes/cm$^2$ at a frequency of approximately 0.1 radians/sec (0.017 Hz), and a range of moduli from approximately $2 \times 10^6$ to $8 \times 10^6$ dynes/cm$^2$ at a frequency of approximately 100 radians/sec (17 Hz) (for example see FIG. 8-16 on p. 173 of *Handbook of PSA Technology* (Donatas Satas, Ed.), 2$^{nd}$ Edition, Van Nostrand Rheinhold, N.Y., 1989). Any of these methods of identifying a PSA may be used to identify suitable PSAs for use in the methods of the present invention.

Examples of PSAs useful in the present invention include rubber based adhesives (e.g., tackified natural rubbers, synthetic rubbers, and styrene block copolymers), (meth)acrylics (i.e., (meth)acrylates), poly(alpha-olefins), polyurethanes, and silicones. Amine containing polymers can also be used which have amine groups in the backbone, pendant thereof, or combinations thereof. A suitable example includes a poly (ethyleneimine).

Some polymers may be chemically modified to include the desired amount of acid or base functionality. Alternatively, the polymers can be made with acid or base-functional monomers. Alternatively or additionally, the PSAs can include acid- or base-functional additives, such as tackifiers, plasticizers, or other additives.

Useful natural rubber PSAs generally contain masticated natural rubber, from 25 parts to 300 parts of one or more tackifying resins to 100 parts of natural rubber, and typically from 0.5 parts to 2.0 parts of one or more antioxidants. Natural rubber may range in grade from a light pale crepe grade to a darker ribbed smoked sheet and includes such examples as CV-60, a controlled viscosity rubber grade and SMR-5, a ribbed smoked sheet rubber grade. Tackifying resins used with natural rubbers generally include but are not limited to wood rosin and its hydrogenated derivatives; terpene resins of various softening points, and petroleum-based resins. Other materials can be added to natural rubber adhesives for special purposes, wherein the additions can include plasticizers, pigments, and curing agents to partially vulcanize the PSA. Examples of acid-modified tackifiers include acid-modified polyhydric alcohol rosin ester tackifiers as described in U.S. Pat. No. 5,120,781.

Another useful class of PSAs is those that include synthetic rubber. Such adhesives are generally rubbery elastomers, which are either self-tacky, or non-tacky that require tackifiers. Examples of acid-modified tackifiers include acid-modified polyhydric alcohol rosin ester tackifiers as described in U.S. Pat. No. 5,120,781. Self-tacky synthetic rubber PSAs include for example, butyl rubber, a copolymer of isobutylene with less than 3 percent isoprene, polyisobutylene, a homopolymer of isoprene, polybutadiene, or styrene/butadiene rubber.

Synthetic rubber PSAs that generally require tackifiers are also usually easier to melt process. They include polybutadiene or styrene/butadiene rubber, from 10 parts to 200 parts of a tackifier, and generally from 0.5 parts to 2.0 parts per 100 parts rubber of an antioxidant. An example of a synthetic rubber is that available from BF Goodrich under the trade name AMERIPOL 101 IA, a styrene/butadiene rubber. Tackifiers that are useful include derivatives of rosins, polyterpenes, C5 aliphatic olefin-derived resins, and C9 aromatic/aliphatic olefin-derived resins.

Styrene block copolymer PSAs generally include elastomers of the A-B or A-B-A type, where A represents a thermoplastic polystyrene block and B represents a rubbery block of polyisoprene, polybutadiene, or poly(ethylene/butylene), and resins. Examples of the various block copolymers useful in block copolymer PSAs include linear, radial, star and tapered styrene-isoprene block copolymers such as those available under the trade names KRATON D 1107P, KRATON G1657, KRATON G 1750X, and KRATON D 1118X from Shell Chemical Co. The polystyrene blocks tend to form domains in the shape of spheroids, cylinders, or plates that causes the block copolymer PSAs to have two phase structures. Resins that associate with the rubber phase generally develop tack in the PSA. Examples of rubber phase associating resins include aliphatic olefin-derived resins, such as those available under the trade names ESCOREZ 1300 and WINGTACK from Goodyear; rosin esters, such as those available under the trade names FORAL and STAYBELITE Ester 10 from Hercules, Inc.; hydrogenated hydrocarbons, such as those available under the trade name ESCOREZ 5000 from Exxon; polyterpenes, such as those available under the trade name PICCOLYTE A; and terpene phenolic resins derived from petroleum or turpentine sources, such as those available under the trade name PICCOFYN A100 from Hercules, Inc. Resins that associate with the thermoplastic phase tend to stiffen the PSA.

In preferred PSAs of the present invention, acrylate and methacrylate monomers and polymers can be used, and are referred to collectively herein as "(meth)acrylate" or "(meth) acrylic" monomers and polymers. (Meth)acrylate polymers may be copolymers, optionally in combination with other, non-(meth)acrylate, e.g., vinyl-unsaturated, monomers. Such polymers and their monomers are well-known in the polymer and adhesive arts, as are methods of preparing the monomers and polymers. One of skill will understand and recognize that such polymers can be useful to impart adhesive properties, and will understand their use in providing an adhesive as described herein.

(Meth)acrylic PSAs generally have a glass transition temperature of about −20° C. or less and may include from 100 to 60 weight percent of a C4-C12 alkyl ester component such as, for example, isooctyl acrylate, 2-ethyl-hexyl acrylate and n-butyl acrylate and from 0 to 40 weight percent of a polar component such as, for example, acrylic acid, methacrylic acid, ethylene, vinyl acetate, N-vinyl pyrrolidone and styrene macromer.

Suitable acidic monomers for preparing (meth)acrylic PSAs include those containing carboxylic acid functionality such as acrylic acid, methacrylic acid, itaconic acid, and the like; those containing sulfonic acid functionality such as 2-sulfoethyl methacrylate; and those containing phosphonic acid functionality. Preferred acidic monomers include acrylic acid and methacrylic acid.

Additional useful acidic monomers in the acidic copolymer include, but are not limited to, those selected from ethylenically unsaturated carboxylic acids, ethylenically unsaturated sulfonic acids, ethylenically unsaturated phosphonic acids, and mixtures thereof. Examples of such compounds include those selected from acrylic acid, methacrylic acid, itaconic acid, fumaric acid, crotonic acid, citraconic acid, maleic acid, oleic acid, B-carboxyethyl acrylate, 2-sulfoethyl methacrylate, styrene sulfonic acid, 2-acrylamido-2-methylpropane sulfonic acid, vinyl phosphonic acid, and the like, and mixtures thereof.

Due to their availability, acidic monomers of the present invention are typically the ethylenically unsaturated carboxylic acids. When even stronger acids are desired, acidic monomers include the ethylenically unsaturated sulfonic acids and ethylenically unsaturated phosphonic acids. Sulfonic and phosphonic acids generally provide a stronger interaction with a basic polymer. This stronger interaction can lead to greater improvements in cohesive strength, as well as higher temperature resistance and solvent resistance of the adhesive.

Suitable basic monomers for preparing (meth)acrylic PSAs include those containing amine functionality such as vinyl pyridine, N,N-diethylaminoethyl methacrylate, N,N-dimethylamino-ethyl methacrylate, N,N-diethylaminoethyl acrylate, N,N-dimethylaminoethyl acrylate, and N-t-butylaminoethyl methacrylate. Preferred basic monomers include N,N-dimethylaminoethyl methacrylate, and N,N-dimethylaminoethyl acrylate.

The (meth)acrylic PSAs may be self-tacky or tackified. Useful tackifiers for (meth)acrylics are rosin esters such as that available under the trade name FORAL 85 from Hercules, Inc., aromatic resins such as that available under the trade name PICCOTEX LC-55WK from Hercules, Inc., aliphatic resins such as that available under the trade name PICCOTAC 95 from Hercules, Inc., and terpene resins such as that available under the trade names PICCOLYTE A-115 and ZONAREZ B-100 from Arizona Chemical Co. Other materials can be added for special purposes, including hydrogenated butyl rubber, pigments, and curing agents to vulcanize the adhesive partially. Examples of acid-modified tackifiers include acid-modified polyhydric alcohol rosin ester tackifiers as described in U.S. Pat. No. 5,120,781.

Poly(alpha-olefin) PSAs, also called a poly(1-alkene) PSAs, generally include either a substantially uncrosslinked polymer or a uncrosslinked polymer that may have radiation activatable functional groups grafted thereon as described in U.S. Pat. No. 5,209,971 (Babu, et al.). The poly(alpha-olefin) polymer may include one or more tackifying materials, not only to improve adhesive properties but also provide the necessary acidic or basic functional groups needed for this application. Tackifying materials are typically resins that are miscible in the poly(alpha-olefin) polymer. The total amount of tackifying resin in the poly(alpha-olefin) polymer ranges from 0 to 150 parts by weight per 100 parts of the poly(alpha-olefin) polymer depending on the specific application. Useful tackifying resins include resins derived by polymerization of C5 to C9 unsaturated hydrocarbon monomers, polyterpenes, synthetic polyterpenes and the like. Examples of such commercially available resins based on a C5 olefin fraction of this type include those available under the trade name WINGTACK from Goodyear Tire and Rubber Co. Other materials can be added for special purposes, including antioxidants, fillers, pigments, and radiation activated crosslinking agents.

Another useful class of PSAs can include polyurethanes. Polyurethanes may be produced by reacting a polyisocyanate with a polyalcohol (polyol). As described herein, a polyisocyanate is a molecule with two or more isocyanate functional groups and a polyalcohol is a molecule with two or more hydroxyl functional groups. The reaction product is a polymer containing urethane linkages. The functional groups can be alkanes, esters, ethers, and other components.

Isocyanates can be classed as aromatic, such as diphenylmethane diisocyanate (MDI) or toluene diisocyanate (TDI); or aliphatic, such as hexamethylene diisocyanate (HDI) or isophorone diisocyanate (IPDI). An example of a polymeric isocyanate is polymeric diphenylmethane diisocyanate, which is a blend of molecules with two-, three-, and four- or more isocyanate groups, with an average functionality of 2.7. Isocyanates can be further modified by partially reacting them with a polyol to form a prepolymer. A quasi-prepolymer is formed when the stoichiometric ratio of isocyanate to hydroxyl groups is greater than 2:1. A true prepolymer is formed when the stoichiometric ratio is equal to 2:1. Important characteristics of isocyanates include the molecular backbone, % NCO content, functionality, and viscosity.

Polyols are distinguished from short chain or low-molecular weight glycol chain extenders and cross linkers such as ethylene glycol (EG), 1,4-butanediol (BDO), diethylene glycol (DEG), glycerine, and trimethylol propane (TMP). Polyols are formed by base-catalyzed addition of propylene oxide (PO), ethylene oxide (EO) onto a hydroxyl or amine containing initiator, or by polyesterification of a di-acid, such as adipic acid, with glycols, such as ethylene glycol or dipropylene glycol (DPG). The choice of initiator, extender, and molecular weight of the polyol greatly affect its physical state, and the physical properties of the polyurethane polymer. Important characteristics of polyols include the molecular backbone, initiator, molecular weight, % primary hydroxyl groups, functionality, and viscosity. Examples of suitable polyurethanes adhesives may include those found in U.S. Pat. No. 7,160,976 (Luhmann et al.), U.S. Pat. No. 6,642,304 (Hansen et. al.) and U.S. Pat. No. 6,518,359 (Clemens et al.).

Silicone PSAs include two major components, a polymer or gum, and a tackifying resin. The polymer is typically a high molecular weight polydimethylsiloxane or polydimethyldiphenylsiloxane, that contains residual silanol functionality (SiOH) on the ends of the polymer chain, or a block copolymer including polydiorganosiloxane soft segments and urea terminated hard segments. The tackifying resin is generally a three-dimensional silicate structure that is endcapped with trimethylsiloxy groups ($OSiMe_3$) and also contains some residual silanol functionality. Examples of tackifying resins include SR 545, from General Electric Co., Silicone Resins Division, Waterford, N.Y., and MQD-32-2 from Shin-Etsu Silicones of America, Inc., Torrance, Calif. Manufacture of typical silicone PSAs is described in U.S. Pat. No. 2,736,721 (Dexter). Manufacture of silicone urea block copolymer PSA is described in U.S. Pat. No. 5,214,119 (Leir et al.).

In some embodiments, the adhesive contains greater than 0.42 mmoles of acidic- or basic-functional groups per gram of PSA that can be neutralized by the MVTR-modifying material. More preferably, the adhesive contains at least 0.69 mmoles of these functional groups per gram of PSA. Even more preferably, the adhesive contains 0.84 mmoles of these functional groups. Even more preferably, the adhesive contains at least 1.3 mmoles of these functional groups. Even more preferably, the adhesive contains at least 1.80 mmoles of these functional groups. Even more preferably, the adhesive contains at least 2.08 mmoles of these functional groups. In most embodiments, the adhesive contains between 1.3 mmoles and 2.5 mmoles of these functional groups.

Preferably, the adhesive should contain no greater than 5.6 mmoles of these functional groups per gram of PSA. More preferably, the adhesive contains no greater than 4.2 mmoles of these functional groups per gram of PSA, and even more preferably no greater than 2.8 mmoles of these functional groups per gram of PSA.

In some embodiments wherein the PSA contains a polymer formed from acidic monomers, the corresponding weight percents may be considered. Preferably, the PSA contains greater than 3 weight percent of a monomer unit in the adhesive polymer that contains acid/base functional groups that can be neutralized by the MVTR-modifying material. More preferably, the PSA contains at least 6 weight percent of these functionalized monomer units. Even more preferably, the PSA contains at least 9 weight percent of these functionalized monomer units. Even more preferably, the PSA contains at least 10 weight percent of these functionalized monomer units. Even more preferably, the PSA contains at least 12 weight percent of these functionalized monomer units.

Preferably, the PSA should contain no greater than 40 weight percent of the functionalized monomer units. More preferably the PSA contains no greater than 30 weight percent, even more preferably no greater than 25 weight percent of the functionalized monomer units and most preferably no greater than 20 based on the total weight of the monomers used in the polymer used to make the PSA. Preferably, such values apply to (meth)acrylate polymers.

In certain embodiments, the PSA may include additional hydrophilic polymer components. These hydrophilic polymer components of the PSA are distinct from plasticizers or other additives that may be used in the adhesive to tackify or otherwise affect properties of the adhesive. The hydrophilic polymer component may be reactive or nonreactive with the adhesive monomers in the PSA. If the hydrophilic polymer is nonreactive (i.e., not incorporated into the polymer chain) the molecular weight of the hydrophilic polymer component is greater than 1000. More preferably, the molecular weight is greater than 2000.

When present in the adhesive, the hydrophilic polymer components are generally present in amounts no greater than 30 weight percent, based on the total weight of the PSA. In those adhesives that include a hydrophilic polymer component, lower concentrations of acid- or basic-functional groups in the PSA may be needed to impact a significant increase in MVTR when an MVTR-modifying material is incorporated into a medical article including the PSA, in comparison to a PSA of the same mass concentration of acid- or basic-functional groups that does not include the hydrophilic polymer components. For example, a PSA with 10 weight percent acid functional groups and 10 weight percent of additional hydrophilic component(s) may show a greater increase in MVTR when exposed to an appropriate MVTR-modifying material by comparison to a PSA with only 10 weight percent acid functional groups and no additional hydrophilic components. The combined weight percent of reactive groups (e.g., acid) and hydrophilic polymer components in the PSA is preferably at least 15%, more preferably at least 20%, and most preferably at least 24% by weight of the PSA. For example, if the adhesive contains 6% acid groups, then the hydrophilic component should be at least 9% by weight, more preferably at least 14% by weight, and most preferably at least 18% by weight. If the adhesive group contains 12 weight % acrylic acid, the hydrophilic component should be at least 3% by weight, more preferably at least 8% by weight, and most preferably at least 12% by weight of the PSA.

In certain embodiments, the ratio of the hydrophobic polymer component(s) in the PSA to the hydrophilic polymer component(s) in the PSA is preferably at least 1.5:1. More preferably at least 1.9:1, even more preferably 2.3:1. In most embodiments, less than 6:1.

In certain embodiments, an exemplary nonreactive hydrophilic polymer component includes one or more poly(alkylene oxide) copolymers. The poly(alkylene oxide) copolymers can be combined with the PSA monomers (e.g., (meth)acrylate monomers or other acidic monomers) or with the copolymer formed from the PSA monomers. The poly(alkylene oxide) copolymers generally do not migrate to the extent of phase separation between the copolymerized acrylate monomers and the poly(alkylene oxide) copolymer. By "phase separation" or "phase separate," it is meant that visible crystallization or liquid regions do not appear in the adhesive solution or bulk adhesive.

In preferred embodiments, the poly(alkylene oxide) copolymers include at least two copolymerized alkylene oxide monomers, at least one of which is hydrophilic and at least one of which is hydrophobic. A preferred copolymer is formed from ethylene oxide and propylene oxide. They can be random, alternating, or block. Preferably, they are block copolymers that include hydrophobic and hydrophilic segments. Particularly useful poly(alkylene oxide) copolymers have a weight average molecular weight of about 1000 to about 15,000, preferably of about 3000 to about 12,000.

Preferred poly(alkylene oxide) copolymers have appreciable water solubility, preferably, at least about 10 parts per 100 parts of water, exhibit surfactant characteristics preferably having an HLB (hydrophilic lipophilic balance) value of about 3 to about 15, and more preferably, about 5 to about 12. Useful poly(alkylene oxide) copolymers have ratios of hydrophilic monomers (e.g., ethylene oxide) to hydrophobic monomers (e.g., propylene oxide) of from about 90:10 to about 10:90, more preferably, from about 80:20 to about 30:70.

Monomers that may be used to make poly(alkylene oxide) copolymers include ethylene oxide and related glycols as a hydrophilic component and propylene oxide, butylene oxide, trimethylene oxide, tetramethylene oxide and the like and related glycols as a hydrophobic component. The poly(alkylene oxide) copolymers may be terminated with lower alkyl groups, amino groups, hydroxyl groups, carboxylic acid groups, aromatic groups, or other nonreactive groups.

Examples of useful poly(alkylene oxide) copolymers include, but are not limited to, those poly(alkylene oxide) copolymers available under the trade designations TETRONIC (tetrafunctional block copolymers derived from sequential addition of propylene oxide and ethylene oxide to ethylene diamine with hydrophilic endblocks) and TETRONIC R (tetrafunctional block copolymers derived from sequential addition of propylene oxide and ethylene oxide to ethylene diamine with hydrophobic endblocks) copolymers available from BASF, Mt. Olive, N.J.; PLURONIC (triblock copolymers with poly(ethylene oxide) end blocks and poly(propylene oxide) midblock) and PLURONIC R (triblock copolymers with poly(propylene oxide) endblocks and poly(ethylene oxide) midblock) copolymers available from BASF; UCON Fluids (random copolymers of ethylene oxide and propylene oxide) available from Union Carbide, Danbury, Conn. Various combinations of poly(alkylene oxide) copolymers can also be used. Preferred nonreactive hydrophilic polymer components are block copolymers of polyethylene glycol and propylene glycol available from BASF, Germany under the trade name PLURONIC.

Preferably, the poly(alkylene oxide) copolymer can be used in an amount of at least about 5 weight percent (wt-%), based on the total weight of the adhesive composition (e.g., the copolymerized (meth)acrylate/hydrophilic acidic comonomers and poly(alkylene oxide) copolymer). More preferably, the poly(alkylene oxide) copolymer is used in an amount of at least about 10 wt-%, and most preferably, at least about 15 wt-%. Preferably, the poly(alkylene oxide) copolymer can be used in an amount of no greater than about 30 wt-%. The amount of poly(alkylene oxide) copolymer required depends upon the type and ratios of the (meth)acrylate and hydrophilic acidic comonomers employed in the polymerizable mixture and the type and molecular weight of the poly(alkylene oxide) copolymer used in the adhesive composition.

In other embodiments, an exemplary reactive hydrophilic polymer component includes a hydrophilic macromolecular monomer which has a vinyl group copolymerizable with the PSA monomers. The hydrophilic macromolecular monomer contains a plurality of hydrophilic sites which impart the required hydrophilicity to the monomer. The hydrophilic macromolecular monomer may be represented by the general Formula I

wherein X is a vinyl group copolymerizable with the PSA monomers, Y is a divalent linking group, and Z is a monovalent polymeric moiety, i.e., containing two or more monomer units, comprising a polyether essentially unreactive under the free radical initiated, copolymerizing conditions employed to form the pressure-sensitive adhesive terpolymer.

The preferred X group is of the general Formula II:

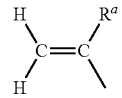

wherein $R^a$ is a hydrogen atom or a methyl group.

The preferred Y group is a

group (i.e., a divalent carbonyl group).

The preferred Z moiety is a monovalent polyether of the general formula III

—W—OR$^b$ wherein R$^b$ is hydrogen, lower alkyl, phenyl, or substituted phenyl; and W is a divalent poly(lower alkylene oxide) group containing 2 to about 250 repeating alkoxy units and selected from the group consisting of a poly(ethylene oxide) radical, a polypropylene oxide) radical, a radical of a copolymer of ethylene oxide and propylene oxide, and a poly(tetramethylene oxide) radical. In a preferred hydrophilic macromonomer, a monovalent polyether of Formula III is bonded covalently to the carbonyl group (i.e., where Y is divalent carbonyl) through a terminal oxygen atom contained in the W moiety.

A variety of hydrophilic macromolecular monomers are available commercially. For example, commercially available monomers which have been found to be suitable are the 2-(2-ethoxyethoxy)ethyl acrylate which is available under the trade designation "SR-256" from Sartomer Company, West Chester, Pa.; the methoxy poly(ethylene oxide) acrylate which is available under the trade designation "No. 8816" from Monomer-Polymer & Dajac Laboratories, Inc., Trevose, Pa.; the methoxy poly(ethylene oxide) methacrylates of 200 Daltons, 400 Daltons, and 1000 Daltons which are available under the trade designations "No. 16664", "No. 16665" and "No. 16666", respectively, from Polysciences, Inc., Warrington, Pa.; and the hydroxy poly(ethylene oxide) methacrylate which is available under the trade designation "No. 16712" from Polysciences, Inc., Warrington, Pa.

Other preferred hydrophilic macromolecular monomers may be prepared using commercially available starting materials and conventional methods, for example, as described in U.S. Pat. No. 4,871,812.

In general, the hydrophilic macromolecular monomer is present in an amount of about 5 to 30% of the total weight of all monomers in the terpolymer. Preferred amounts for the monomers are about 10 to 20% by weight based upon the total amount of all monomers in the terpolymer.

Preferred polymers included in the PSA are (meth)acrylate polymers. Particularly useful adhesive composition include a 65:15:20 2-ethylhexylacrylate: acrylic acid copolymer blended with a nonreactive polyalkylene oxide copolymer under the trade name PLURONIC. Other suitable examples include a 90:10 iso-octyl acrylate: acrylic acid copolymer, a 70:15:15 isooctyl acrylate: ethyleneoxide acrylate: acrylic acid terpolymer, and a 25:69:6 2-ethylhexylacrylate: butyl acrylate: acrylic acid terpolymer. Useful adhesives can be any of those that are compatible with skin and useful for wound dressings, such as those disclosed in U.S. Pat. No. Re. 24,906 (Ulrich), U.S. Pat. No. 5,849,325 (Heinecke, et al.), and U.S. Pat. No. 4,871,812 (Lucast, et. al.) (water-based and solvent-based adhesives); U.S. Pat. No. 4,833,179 (Young, et al.) (hot-melt adhesives); U.S. Pat. No. 5,908,693 (Delgado, et al.) (microsphere adhesives); U.S. Pat. No. 6,171,985 and U.S. Pat. No. 6,083,856 (both to Joseph, et al.) (low trauma fibrous adhesives); and, U.S. Pat. No. 6,198,016 (Lucast, et al.), U.S. Pat. No. 6,518,343 (Lucast, et al.), and U.S. Pat. No. 6,441,082 (Gieselman) (wet-skin adhesives). Inclusion of medicaments or antimicrobial agents in the adhesive is also contemplated, as described in U.S. Pat. Nos. 4,310,509 and 4,323,557.

Scaffold

When used, the scaffold 22, as shown, for example, in FIG. 2, may include a nonwoven material. Suitable nonwoven materials include, but are not limited to, TENCEL/Polyester nonwovens, and Lycocell-Rayon/Polyester Nonwovens both available from Ahlstrom Green Bay, Green Bay, Wis. Other suitable nonwovens include cotton spun laced nonwovens available from Unitika Ltd., Japan. In another embodiment, the scaffold 22 is a TMED011 nonwoven available from National Nonwovens Co., East Hampton, Mass. The scaffold 22 may also include wovens, knitted fabrics, foams, porous films, gels, hydrocolloids, cellulosic material, carboxyl methyl cellulose, alginates, and water-swellable or water-absorbable adhesives. In preferred embodiments, the scaffold 22 is capable of absorbing moisture.

Filtration Layer

When used, the filtration layer 32, as shown for example in FIG. 3b, may include one or more nonwoven layers. Suitable nonwoven materials include, but are not limited to, TENCEL/Polyester nonwovens, and Lycocell-Rayon/Polyester Nonwovens both available from Ahlstrom Green Bay, Green Bay, Wis. Other suitable nonwovens include cotton spun laced nonwovens available from Unitika Ltd., Japan. In another embodiment, the filtration layer 32 is a TMED011 nonwoven available from National Nonwovens Co., East Hampton, Mass. The filtration layer may also be composed of wovens, knitted fabrics, foams, porous films, gels, hydrocolloids, cellulosic material, alginates, and water-swellable or water-absorbable adhesives.

Suitable examples of a filtration layer selected for filtration purposes include filtration membranes, filtration materials, non wovens, wovens, gels and foams.

Absorbent Layer

When used, the absorbent layer can be manufactured of any of a variety of materials including, but not limited to, woven or nonwoven cotton or rayon. Absorbent layer is useful for containing a number of substances, optionally including antimicrobial agents, drugs for transdermal drug delivery, chemical indicators to monitor hormones or other substances in a patient, etc.

The absorbent layer may include a hydrocolloid composition, including the hydrocolloid compositions described in U.S. Pat. Nos. 5,622,711 and 5,633,010. Absorbent materials may also be chosen from other synthetic and natural materials including polymer gels, foams, collagens, carboxymethyl cellulose fibers, alginates, nonwovens, or woven materials. In some embodiments, the absorbent layer may include a polymeric fabric, a polymeric foam, and combinations thereof. For example, the polymeric fabric may be a nonwoven and the polymeric foam may be the foam used in the TEGADERM foam adhesive dressing available from 3M Company, St. Paul, Minn. In certain embodiments, the polymeric foam is a polyurethane foam.

Facing Layer

When used, the facing layer is preferably soft, flexible, conformable, non-irritating and non-sensitizing. Any of a variety of polymers may be used including polyurethane, polyethylene, polypropylene, polyamide or polyester materials. Further, the facing layer may be in the form of moisture vapor permeable films, perforated films, woven-, non-woven or knit webs or scrims.

The facing layer may also include an adhesive laminated on the surface of the filtration layer facing the wound or other target site. In such an embodiment, the second adhesive may be an acrylic, silicone gel, polyurethane, or rubber based adhesive. Exemplary embodiments of suitable facing layers and adhesives may be found, for example, in U.S. Pat. No. 7,612,248 to Burton et al. The facing layer may also include an additional adhesive on the surface of the facing layer opposite the target site.

Carrier Films

Carrier films (e.g., as shown in FIG. 11) suitable for use with the invention can be made of kraft papers, polyethylene, polypropylene, polyester or composites of any of these materials. The films are preferably coated with release agents such as fluorochemicals or silicones. For example, U.S. Pat. No. 4,472,480 describes low surface energy perfluorochemical liners. The liners are papers, polyolefin films, or polyester films coated with silicone release materials. Examples of commercially available silicone coated release papers are POLYSILK™, silicone release papers available from Rexam Release (Bedford Park, Ill.) and silicone release papers supplied by Loparex Inc. (Willowbrook, Ill.).

Objects and advantages of this invention are further illustrated by the following examples, but the particular materials and amounts thereof recited in these examples, as well as other conditions and details, should not be construed to unduly limit this invention. Unless otherwise indicated, all parts and percentages are by weight.

Test Methods

1. Moisture Vapor Transmission Rate—Upright (Dry) MVTR

A. For Samples That Did Not Contain A Foam Component

The upright MVTR was measured according to ASTM E-96-80 using a modified Payne cup method. A 3.8 cm diameter sample was placed between adhesive-containing surfaces of two foil adhesive rings, each having a 5.1 cm$^2$ elliptical opening. The holes of each ring were carefully aligned. Finger pressure was used to form a foil/sample/foil assembly that was flat, wrinkle free, and had no void areas in the exposed sample.

A 120-ml glass jar was filled with approximately 50 g of tap water that contained a couple drops of 0.02% (w/w) aqueous Methylene Blue USP (Basic Blue 9, C.I.52015) solution, unless specifically stated in an example. The jar was fitted with a screw-on cap having a 3.8 cm diameter hole in the center thereof and with a 4.45 cm diameter rubber washer having an approximately 3.6 cm hole in its center The rubber washer was placed on the lip of the jar and foil/sample/foil assembly was placed backing side down on the rubber washer. The lid was then screwed loosely on the jar.

The assembly was placed in a chamber at 40° C. and 20% relative humidity for four hours. At the end of four hours, the cap was tightened inside the chamber so that the sample was level with the cap (no bulging) and the rubber washer was in proper seating position.

EXAMPLES

TABLE 1

| Glossary of Components | | |
|---|---|---|
| Material/Trade Name | Description | Source/Address |
| 3M TEGADERM 9548HP | Transparent Film Dressing | 3M Company, St. Paul, MN |
| 3M TEGADERM 90612 | Foam Adhesive Dressing | 3M Company, St. Paul, MN |
| ESTANE 58237 Resin | Polyurethane resin | Lubrizol, Wickliffe, OH |
| 70/30 TENCEL/Polyester Non-woven | Grade 240 (SX-33) spunlaced non-woven, 40 g/m$^2$, 24 mesh apertured; 70/30 TENCEL/polyester | Ahlstrom, Green Bay, WI |
| 30/70 Lyocell-Rayon/Polyester Non-woven | Grade SX-473 spunlaced, non-apertured non-woven, 45 g/m$^2$ | Ahlstrom, Green Bay, WI |
| Na$_3$C$_6$H$_5$O$_7$—2H$_2$O | Sodium Citrate Dihydrate | Mallinckrodt, Phillipsburg, NJ |
| C$_6$H$_8$O$_7$ | Citric acid, anhydrous, USP grade | Spectrum Chemical, Gardena, CA or VWR International, West Chester, PA |
| COTTOASE | 100% cotton, spunlaced non-woven, 50 gsm | Unitika, Japan |
| NaOH | 50% (w/w) solution diluted to desired concentration with USP Sterile water | J. T. Baker Phillipsburg, NJ |
| Water | USP Sterile water | Baxter, Deerfield, IL |
| Na$_2$CO$_3$—H$_2$O | Sodium carbonate monohydrate | Mallinckrodt, Phillipsburg, NJ or Fisher Scientific, Fair Lawn, NJ |
| NaHCO$_3$ | Sodium bicarbonate | VWR International, West Chester, PA |
| CH$_3$N(C$_2$H$_4$OH)$_2$ | Methyl diethanolamine (MDEA) | Dow, Midland, MI |
| K$_2$CO$_3$ | Potassium Carbonate, anhydrous, ACS grade | VWR International, West Chester, PA |
| KHCO$_3$ | Potassium bicarbonate, USP grade | Mallinckrodt, Phillipsburg, NJ |

The foil sample assembly was removed from the chamber and weighed immediately to the nearest 0.01 gram for an initial dry weight, W1. The assembly was then returned to the chamber for at least 18 hours, the exposure time T1 in hours, after which it was removed and weighed immediately to the nearest 0.01 g for a final dry weight, W2. The MVTR in grams of water vapor transmitted per square meter of sample area per 24 hours can then be calculated using the following formula.

$$\text{Upright (Dry) MVTR} = (W1-W2) \times (4.74 \times 10^4)/T1$$

B. For Samples That Did Contain A Foam Component

The upright MVTR procedure for these samples was identical to that described above except the test sample size was a 4.45 cm diameter sample and the sample was sandwich between two LEXAN (polycarbonate) washers (4.47 cm diameter with 2.54 cm hole in the middle), instead of the foil adhesive rings.

2. Moisture Vapor Transmission Rate—Inverted (Wet) MVTR

The inverted MVTR was measured using the following test procedure. After obtaining the final "dry" weight, W2, as described for the upright MVTR procedures, the assembly was returned to the chamber for a least 18 additional hours of exposure time, T2, with the jars inverted so that the tap water was in direct contact with the test sample. The sample was then removed from the chamber and weighed to the nearest 0.01 gram for a final wet weight, W3. The inverted wet MVTR in grams of water vapor transmitted per square meter of sample area per 24 hours can then be calculated using the following formula.

$$\text{Inverted (Wet) MVTR} = (W2-W3) \times (4.74 \times 10^4)/T2$$

Multiple samples of the Examples below were measured for Upright (Dry) and Inverted (Wet) MVTR. The average results are reported below, followed by the standard deviation (+/−) of the multiple samples.

3. Adhesion To Steel

The Adhesion to Steel test was performed in accordance with ASTM D3330M at 30.5 cm/min and 180 degree peel.

Example 1

Comparative

A 40 g/m² 70/30 (w/w) TENCEL/Polyester Grade 240 (SX-33) spunlaced non-woven (Ahlstrom Green Bay, Green Bay, Wis.) was laminated by hand to the adhesive side of a 3M TEGADERM 9548HP dressing and allowed to sit for approximately 30 days prior to testing. Five specimens from the sample were tested for both upright and inverted Moisture Vapor Transmission Rates (MVTR). The average upright MVTR and inverted MVTR values were 1150+/−100 g/m²/24 hours and 2340+/−190 g/m²/24 hours, respectively.

Example 2

Comparative

The non-woven from Example 1 was saturated with a 2.6% (w/w) aqueous solution of sodium citrate dehydrate and dried in a laboratory scale forced air oven (Memmert Universal Oven; Wisconsin Oven Company, East Troy, Wis.) at 80° C. for 30 minutes. The coating weight of sodium citrate dehydrate on the non-woven was 15 g/m². This coated non-woven was then laminated by hand to the adhesive side of a 3M TEGADERM 9548HP dressing. Samples were allowed to sit for approximately 30 days prior to testing. For the five specimens tested from the sample, the average upright MVTR and inverted MVTR values were 1000+/−30 g/m²/24 hours and 2350+/−90 g/m²/24 hours, respectively.

Example 3

Comparative

A 100% cotton spunlaced non-woven (COTTOASE) was saturated with a 5.4% (w/w) aqueous solution of citric acid, dried in an oven at 85° C. for approximately 30 minutes, and then laminated by hand to the adhesive side of a 3M TEGADERM 9548HP dressing. The samples were allowed to sit for 3 days prior to testing. The average upright MVTR and inverted MVTR values for the four test specimens were 1180+/−60 g/m²/24 hours and 1720+/−40 g/m²/24 hours, respectively.

Example 4

The non-woven from Example 1 was saturated with a 0.15 M aqueous solution of sodium hydroxide, and then dried in an oven at 75° C. for 30 minutes prior to lamination to the adhesive side of the dressing. The coating weight of sodium hydroxide on the non-woven was measured at 5 g/m². This coated non-woven was then laminated by hand to the adhesive side of a 3M TEGADERM 9548HP dressing. Four test specimens from the sample were tested two days after the lamination step for both upright and inverted Moisture Vapor Transmission Rates (MVTR). The average upright MVTR and inverted MVTR values were 1210+/−50 g/m²/24 hours and 11400+/−1800 g/m²/24 hours, respectively.

Example 5

The non-woven from Example 1 was saturated with a 0.30 M aqueous solution of sodium hydroxide, and then dried in an oven at 75° C. for 30 minutes prior to lamination to the adhesive side of the dressing. The coating weight of sodium hydroxide on the non-woven was measured at 7 g/m². This coated non-woven was then laminated by hand to the adhesive side of a 3M TEGADERM 9548HP dressing. Four test specimens from the sample were tested two days after the lamination step for both upright and inverted Moisture Vapor Transmission Rates (MVTR). The average upright MVTR and inverted MVTR values were 1280+/−60 g/m²/24 hours and 16900+/−740 g/m²/24 hours, respectively.

Example 6

The non-woven from Example 1 was dip coated in a 4.0% (w/w) aqueous solution of sodium carbonate monohydrate at a rate of 13 feet/min (3.96 meter/min) and dried in a pilot scale forced air oven at approximately 105° C. for about 5 minutes. The coating weight of sodium carbonate monohydrate on the non-woven was 16.3 g/m². This coated non-woven was then laminated by hand to the adhesive side of a 3M TEGADERM 9548HP dressing. For the five specimens tested, the average upright MVTR and inverted MVTR values were 1070+/−40 g/m²/24 hours and 20800+/−980 g/m²/24 hours, respectively.

Example 7

A 100% cotton spunlaced non-woven (COTTOASE) was saturated with a 3.5% (w/w) aqueous solution of sodium bicarbonate, dried in an oven at 45° C. until dry and then laminated by hand to the adhesive side of a 3M TEGADERM 9548HP dressing. The samples were allowed to sit for 3 days prior to testing. The average upright MVTR and inverted MVTR values were 1340+/−100 g/m²/24 hours and 19100+/−870 g/m²/24 hours, respectively.

Example 8

The non-woven from Example 1, a 40 g/m² 70/30 (w/w) TENCEL/Polyester spunlaced non-woven, was saturated with a 5.3% (w/w) aqueous solution of potassium carbonate, and then dried at 85° C. for 40 minutes. The coating weight of potassium carbonate on the non-woven was 46 g/m². This coated non-woven was then laminated by hand to the adhesive side of a 3M TEGADERM 9548HP dressing. The samples were tested four days after the lamination step. The average upright MVTR and inverted MVTR values of four test specimens were 1390+/−40 g/m²/24 hours and 20700+/−530 g/m²/24 hours, respectively.

Example 9

The 40 g/m² 70/30 (w/w) TENCEL/Polyester spunlaced non-woven from Example 1 was saturated with a 3.7% (w/w) aqueous solution of potassium bicarbonate, and then dried at 75° C. for 30 minutes. The coating weight of potassium bicarbonate on the non-woven was 24 g/m². This coated non-woven was then laminated by hand to the adhesive side of a 3M TEGADERM 9548HP dressing. The samples were tested five days after the lamination step. The average upright MVTR and inverted MVTR values of four test specimens were 1650+/−20 g/m²/24 hours and 20300+/−610 g/m²/24 hours, respectively.

Example 10

The 40 g/m² 70/30 (w/w) TENCEL/Polyester spunlaced non-woven from Example 1 was saturated with a solution of 2.6% (w/w) aqueous solution of sodium carbonate monohydrate, and then dried in a laboratory scale forced air oven (Memmert Universal Oven; Wisconsin Oven Company, East Troy, Wis.) at 80° C. for 30 minutes. The coating weight of sodium carbonate monohydrate on the non-woven was 8.3 g/m². This coated non-woven was laminated by hand to the adhesive side of a 3M TEGADERM 9548HP dressing. Two layers of untreated non-woven were placed on top of the coated layer of non-woven that was laminated to the adhesive side of the dressing. Four specimens from the samples were tested five days after the lamination step. The average upright MVTR and inverted MVTR values of four test specimens were 1190+/−100 g/m²/24 hours and 16700+/−1700 g/m²/24 hours, respectively.

Example 11

This example was prepared like Example 10 except the two layers of untreated non-woven were placed between the adhesive and the sodium carbonate monohydrate treated layer of non-woven. The average upright MVTR and inverted MVTR values of test specimens were 1240+/−280 g/m²/24 hours and 9150+/−1280 g/m²/24 hours, respectively.

Example 12

This example was prepared like Example 6 except an additional layer of non-woven that was treated with a 2.6% (w/w) aqueous solution of citric acid and then dried at 80° C. for 30 minutes was placed on top the sodium carbonate monohydrate treated non-woven layer. The addition of the citric acid treated non-woven layer occurred eight days after the lamination of the sodium carbonate monohydrate sample to the adhesive side of the dressing. The coating weight of citric acid on the non-woven was 18.5 g/m². Five test specimens from the samples were tested 24 days after the addition of the citric acid treated non-woven layer to the sample. The average upright MVTR and inverted MVTR values of test specimens were 1080+/−30 g/m²/24 hours and 9880+/−2660 g/m²/24 hours, respectively.

Example 13

This example was prepared by cutting an approximately 7.5 cm×7.5 cm foam sample from a 90612 3M TEGADERM Foam Adhesive Dressing (3M Company, St. Paul, Minn.) such that the foam piece freely separates from all other parts of the dressing. One side of this foam piece was then coated with a 5.5% (w/w) aqueous solution of sodium carbonate monohydrate and dried at 80° C. for 40 minutes. The coating weight of sodium carbonate monohydrate on the foam piece was approximately 19 g/m². The coated side of the foam piece was then laminated by hand to the adhesive side of a 3M TEGADERM 9548HP Transparent Dressing. Four test specimens were tested 5 days after the lamination step. The average upright MVTR and inverted MVTR values of test specimens were 900+/−60 g/m²/24 hours and 7840+/−1600 g/m²/24 hours, respectively.

Example 14

For this example, an approximately 25 micron thick layer of pressure sensitive adhesive of 70/15/15 ratio of IOA/AA/EOA on paper liner as described in U.S. Pat. No. 4,737,410 Example 31 with less than 1% polyethyloxazoline was used. An approximately 25 micron urethane film (ESTANE 58237 resin; Lubrizol Corporation, Wickliffe, Ohio) was extruded over the aforementioned adhesive layer using the method as described in U.S. Pat. No. 4,499,896 to form the adhesive/film laminate on liner. The non-woven from Example 1, a 40 g/m² 70/30 (w/w) TENCEL/Polyester spunlaced non-woven, was saturated with a 2.6% (w/w) aqueous solution of sodium carbonate monohydrate prior to drying it in the oven This saturated non-woven was then dried at 85° C. for approximately 30 minutes. The coating weight of the sodium carbonate monohydrate on the non-woven was 8 g/m². The average upright MVTR and inverted MVTR values of five test specimens were 1660+/−60 g/m²/24 hours and 18800+/−860 g/m²/24 hours, respectively.

Example 15

Comparative

For this example, the adhesive from Example 14 and urethane film from Example 14 were constructed as described in Example 14. The non-woven from Example 1, a 40 g/m² 70/30 (w/w) TENCEL/Polyester spunlaced non-woven, was directly laminated by hand to the adhesive side of the laminate without the addition of any MVTR-modifying material. The average upright MVTR and inverted MVTR values of up to five test specimens were 1150+/−30 g/m$^2$/24 hours and 2250+/−250 g/m$^2$/24 hours, respectively.

Example 16

Comparative

The samples were prepared by first laminating the adhesive from Example 14 to a 25 micron ESTANE 58237 film on paper carrier using a XRL 120 roll laminator (Western Magnum; El Segundo, Calif.) set at approximately 20 psig (1.4 bar). A second layer of the adhesive was then laminated using the roll laminator to the first adhesive layer in order to double the thickness of the adhesive. A piece of untreated non-woven used in Example 1 was then laminated by hand to the adhesive six days prior to testing. The average upright MVTR and inverted MVTR values of four test specimens were 690+/−40 g/m$^2$/24 hours and 1170+/−210 g/m$^2$/24 hours, respectively.

Example 17

The samples were prepared like Example 16 except that the non-woven was saturated with a 2.6% (w/w) aqueous solution of sodium carbonate monohydrate. This saturated non-woven was then dried at 85° C. for approximately 30 minutes for a dried coating weight of 11 g/m$^2$. The average upright MVTR and inverted MVTR values of four test specimens were 1235+/−40 g/m$^2$/24 hours and 20700+/−500 g/m$^2$/24 hours, respectively.

Example 18

The sample was prepared similar to Example 14, except: 1) the non-woven was dip coated into a 3% (w/w) aqueous solution of sodium carbonate monohydrate at 13 feet/min (3.96 meters/min) and dried in a pilot scale forced air oven at approximately 105° C. for about 5 minutes; 2) a second absorbent non-woven layer (National Non-wovens; Easthampton, Mass.) was placed on top of the sodium carbonate monohydrate treated non-woven layer; and 3) a third absorbent layer (polyurethane foam used in 3M TEGADERM Foam Adhesive Dressings) was then placed on top of second absorbent non-woven layer. The coating weight of sodium carbonate monohydrate on the treated non-woven was 12.6 g/m$^2$. These samples were also gamma irradiated at 35.8-41.4 kGy. The samples were tested 12 days after construction and 8 days after gamma irradiation. The average upright MVTR and inverted MVTR values of four test specimens were 1200+/−60 g/m$^2$/24 hours and 16000+/−2800 g/m$^2$/24 hours, respectively.

Example 19

The example was prepared and conducted identical to Example 18 except the test solution used for the MVTR tests was a 90/10 (w/w) mixture of phosphate buffered saline and Adult Bovine Serum instead of tap water. The phosphate buffered saline was P-3813 at a pH of 7.4 (Sigma-Aldrich; St. Louis, Mo.). The Bovine Serum was product B9433 (Sigma-Aldrich; St. Louis, Mo.). The average upright MVTR and inverted MVTR values of four test specimens were 1080+/−130 g/m$^2$/24 hours and 11200+/−1200 g/m$^2$/24 hours, respectively.

Example 20

Comparative

An approximately 18 micron thick layer of 90/10 (w/w) IOA/AA pressure sensitive adhesive prepared as described in U.S. Pat. No. 4,737,410 Example 11 was used. The adhesive was pressure laminated using the XRL 120 roll laminator to an approximately 25 micron thick polyurethane ESTANE 58237 film on a paper carrier. The non-woven from Example 1, a 40 g/m$^2$ 70/30 (w/w) TENCEL/Polyester spunlaced non-woven, was then laminated by hand to the adhesive side of the adhesive/film laminate. Samples were tested six days after lamination of the non-woven to the adhesive. The average upright MVTR and inverted MVTR values of four test specimens were 820+/−10 g/m$^2$/24 hours and 1180+/−20 g/m$^2$/24 hours, respectively.

Example 21

An approximately 18 micron thick layer 90/10 (w/w) IOA/AA pressure sensitive adhesive was pressure laminated using the XRL 120 roll laminator to an approximately 25 micron thick polyurethane ESTANE 58237 film on a paper carrier. The non-woven from Example 1, a 40 g/m$^2$ 70/30 (w/w) TENCEL/Polyester spunlaced non-woven, was treated with sodium carbonate monohydrate, dried at 85° C. for approximately 30 minutes for a dried coating weight of 11 g/m$^2$. The non-woven was then laminated by hand to the adhesive side of the adhesive/film laminate. Samples were tested six days after lamination of the non-woven to the adhesive. The average upright MVTR and inverted MVTR values of four test specimens were 900+/−30 g/m$^2$/24 hours and 1440+/−50 g/m$^2$/24 hours, respectively.

Example 22

Comparative

An 18 micron thick pressure sensitive adhesive on polyester liner was made in a manner described in U.S. Pat. No. 4,737,410, but with the following monomers and ratios: 25/69/6 2-EHA/BA/AA (w/w/w). The pressure sensitive adhesive was pressure laminated using a roll laminator to an approximately 25 micron thick polyurethane ESTANE 58237 film on paper carrier. The non-woven from Example 1, a 40 g/m$^2$ 70/30 (w/w) TENCEL/Polyester spunlaced non-woven, was then laminated by hand to the adhesive side of the adhesive/film laminate. Samples were tested six days after lamination of the non-woven to the adhesive. The average upright MVTR and inverted MVTR values of four test specimens were 1500+/−30 g/m$^2$/24 hours and 2400+/−160 g/m$^2$/24 hours, respectively.

Example 23

The PSA of Example 22 was pressure laminated using a roll laminator to an approximately 25 micron thick polyurethane ESTANE 58237 film on paper carrier. The non-woven from Example 1, a 40 g/m$^2$ 70/30 (w/w) TENCEL/Polyester spunlaced non-woven, was treated with sodium carbonate monohydrate, dried at 85° C. for approximately 30 minutes, for a dried coating weight of 11 g/m$^2$. The non-woven was then laminated by hand to the adhesive side of the adhesive/film laminate. Samples were tested six days after lamination of the non-woven to the adhesive. The average upright MVTR and inverted MVTR values of four test specimens were 1570+/−80 g/m²/24 hours and 2540+/−60 g/m²/24 hours, respectively.

Example 24

Comparative

The grade SX-473 non-woven (Ahlstrom, Greenbay, Wis.) was laminated to an approximately 38 micron thick layer 90/10 (w/w) IOA/AA pressure sensitive adhesive using the XRL 120 roll laminator. Samples were tested eight days after lamination of the non-woven to the adhesive. The average upright MVTR of five test specimens was 1390+/−420 g/m²/24 hours. Inverted MVTR was not measure because specimens would have leaked during the test.

Example 25

This example was prepared like Example 24 except the grade SX-473 non-woven was saturated with a 3.4% (w/w) aqueous solution of sodium bicarbonate and dried at 50° C. for 90 minutes and then 35° C. overnight. The coating weight of sodium bicarbonate was approximately 24 g/m². This treated non-woven was laminated to the adhesive in Example 24. Samples were tested eight days after lamination of the non-woven to the adhesive. The average upright MVTR of five test specimens was 1860+/−260 g/m²/24 hours.

Example 26

Comparative

The grade SX-473 non-woven (Ahlstrom, Greenbay, Wis.) was roll laminated to an approximately 38 micron thick layer of the PSA from Example 22, 25/69/6 (w/w/w) 2-EHA/BA/AA. Samples were tested eight days after lamination of the non-woven to the adhesive. The average upright MVTR of five test specimens was 1390+/−420 g/m²/24 hours. Inverted MVTR was not measure because specimens would have leaked during the test.

Example 27

This sample was prepared and tested like Example 26 except the non-woven was saturated with a 3.4% (w/w) aqueous solution of sodium bicarbonate and dried at 50° C. for 90 minutes and then 35° C. overnight. The coating weight of sodium bicarbonate was approximately 24 g/m². This treated non-woven was hand laminated to the adhesive. The average upright MVTR of five test specimens was 1680+/−250 g/m²/24 hours.

Example 28

Comparative

The adhesive on liner in Example 14 was treated with droplets of sterile water via spraying with a spray bottle such that approximately 40% of the adhesive was covered with droplets and then the sample dried in a laboratory oven at 75° C. for 35 minutes. A 25 micron thick polyurethane ESTANE 58237 film on a paper carrier was then laminated to the water treated side of the adhesive on liner using the XRL 120 laminator. Samples of the adhesive/film laminate were tested six days after the lamination step. The average upright MVTR and inverted MVTR values of five test specimens were 940+/−30 g/m²/24 hours and 1600+/−490 g/m²/24 hours, respectively. The average adhesion to steel of 2.54 cm wide samples was measured to be 294+/−9 g/cm.

Example 29

This sample was prepared like Example 28 except the adhesive on liner was treated with droplets of an aqueous solution of 1.5% (w/w) sodium carbonate monohydrate via a syringe prior to drying. Each droplet weighed approximately 80 mg. The average upright MVTR and inverted MVTR values of five test specimens were 1530+/−40 g/m²/24 hours and 9460+/−950 g/m²/24 hours, respectively. The average adhesion to steel of 2.54 cm wide samples was measured to be 166+/−16 g/cm.

Example 30

Comparative

For this example, an approximately 28 micron thick layer adhesive of 90/10 (w/w) IOA/AA on polyester liner was laminated to an approximately 25 micron thick polyurethane ESTANE 58237 film on a paper carrier using the XRL 120 laminator. The non-woven from Example 1, a 40 g/m² 70/30 (w/w) TENCEL/Polyester spunlaced non-woven, was directly laminated by hand to the adhesive side of the laminate without MVTR-modifying material and the paper carrier was removed from the film side of the sample. Four specimens were tested six days after construction of the samples. The average upright MVTR and inverted MVTR values were 640+/−15 g/m²/24 hours and 1090+/−30 g/m²/24 hours, respectively.

Example 31

Comparative

The samples were prepared like Example 30 except that the adhesive was only 18 microns thick. The average upright MVTR and inverted MVTR values of four test specimens were 820+/−15 g/m²/24 hours and 1180+/−20 g/m²/24 hours, respectively.

Example 32

The samples were prepared like Example 30 except that: (1) the non-woven was saturated with an aqueous solution of 2.5% (w/w) of sodium carbonate monohydrate, dried at 85° C. for approximately 30 minutes for a coating weight of sodium carbonate monohydrate on the dried non-woven of 11 g/m²; and (2) the adhesive was only 18 microns thick. The average upright MVTR and inverted MVTR values of four test specimens were 900+/−30 g/m²/24 hours and 1440+/−50 g/m²/24 hours, respectively.

Example 33

Comparative

This sample was prepared like example 30 (no treatment on non-woven with MVTR-modifying material) except that the polyurethane ESTANE 58237 film on paper carrier was laminated to an 18 micron thick layer of the PSA of Example 22, which was 25/69/6 2-EHA/BA/AA (w/w/w). Four specimens were tested six days after construction of the samples. The average upright MVTR and inverted MVTR values were 1500+/−30 g/m²/24 hours and 2400+/−160 g/m²/24 hours, respectively.

Example 34

The samples were prepared like Example 33 except that the non-woven was saturated with an aqueous solution of 2.5% (w/w) of sodium carbonate monohydrate, dried at 85° C. for approximately 30 minutes for a coating weight of 11 g/m². The average upright MVTR and inverted MVTR values of four test specimens were 1570+/−80 g/m²/24 hours and 2540+/−60 g/m²/24 hours, respectively.

Example 35

Comparative

An approximately 22 micron thick layer of 90/10 (w/w) IOA/AA pressure sensitive adhesive was pressure laminated to an approximately 25 micron thick polyurethane ESTANE 58237 film on a paper carrier. The untreated non-woven from Example 1, a 40 g/m² 70/30 (w/w) TENCEL/Polyester spunlaced non-woven was then laminated by hand to the adhesive side of the adhesive/film laminate and the paper carrier was removed from the film side of the sample. Samples were tested seven days after lamination of the non-woven to the adhesive. The average upright MVTR and inverted MVTR values of four test specimens were 920+/−10 g/m²/24 hours and 1460+/−140 g/m²/24 hours, respectively.

Example 36

The samples were prepared and tested like Example 35 except the non-woven was saturated with a 3% (w/w) aqueous solution of sodium carbonate monohydrate, dried at 75° C. for 30 minutes, prior to lamination to the adhesive. The coating weight of the sodium carbonate monohydrate on the non-woven was approximately 11 g/m². The average upright MVTR and inverted MVTR values of four test specimens were 1040+/−60 g/m²/24 hours and 1570+/−100 g/m²/24 hours, respectively.

Example 37

Comparative

An approximately 22 thick pressure sensitive adhesive made in a manner described in U.S. Pat. No. 4,737,410, but with the following monomers and ratios: 46.5/46/7.5 ratio of 2-EHA/BA/AA (w/w/w) was pressure laminated to an approximately 25 micron thick polyurethane ESTANE 58237 film on a paper carrier. The untreated non-woven from Example 1, a 40 g/m² 70/30 (w/w) TENCEL/Polyester spunlaced non-woven was then laminated by hand to the adhesive side of the adhesive/film laminate and the paper carrier was removed from the film side of the sample. Samples were tested seven days after lamination of the non-woven to the adhesive. The average upright MVTR and inverted MVTR values of four test specimens were 1560+/−30 g/m²/24 hours and 2470+/−110 g/m²/24 hours, respectively.

Example 38

The samples were prepared and tested like Example 37 except the non-woven was saturated with a 3% (w/w) aqueous solution of sodium carbonate monohydrate dried at 85° C. for approximately 30 minutes for a coating weight of 11 g/m². The average upright MVTR and inverted MVTR values of four test specimens were 1590+/−10 g/m²/24 hours and 2590+/−130 g/m²/24 hours, respectively.

Example 39

Comparative with Amine Adhesive

An amine based adhesive was made polymerizing a mixture of 2-EHA (90 g) acrylamide (4 g), dimethyaminoethly methacrylate, DMAEMA (6 g) in ethyl acetate (122 g) at 55° C. for 16 hours followed by 65° C. for 8 hours. The resulting adhesive in solution was coated on to a release liner and dried which resulted in an approximately 25 micron thick adhesive layer on liner. This adhesive was then pressure laminated to a film of approximately 25 micron thick polyurethane ESTANE 58237 film on a paper carrier. The non-woven from Example 1, a 40 g/m² 70/30 (w/w) TENCEL/Polyester spunlaced non-woven, was then laminated by hand to the adhesive side of the adhesive/film laminate, seven days prior to testing. The average upright MVTR and inverted MVTR values of five test specimens were 950+/−40 g/m²/24 hours and 1520+/−210 g/m²/24 hours, respectively.

Example 40

Comparative Base with MVTR-Modifying Material and Base Adhesive

This sample was prepared and tested like Example 39 except the non-woven was treated with MVTR-modifying material, sodium carbonate monohydrate, dried at 85° C. for approximately 30 minutes for a coating weight of 12 g/m² prior to lamination to the adhesive. The average upright MVTR and inverted MVTR values of five test specimens were 990+/−30 g/m²/24 hours and 1590+/−300 g/m²/24 hours, respectively.

Example 41

Comparative

A 33% solids adhesive solution in ethyl acetate of the adhesive from Example 14 was coated onto a release liner and dried to a thickness of 23 microns. The adhesive was pressure laminated to a film of approximately 25 micron thick polyurethane ESTANE 58237 film on a paper carrier. The non-woven from Example 1, a 40 g/m² 70/30 (w/w) TENCEL/Polyester spunlaced non-woven, was then laminated by hand to the adhesive side of the adhesive/film construction at least seven days prior to testing. The average upright MVTR and inverted MVTR values of four test specimens were 1300+/−30 g/m²/24 hours and 1950+/−110 g/m²/24 hours, respectively. The average adhesion to steel of five test specimens that were 2.54 cm wide was measured to be 540+/−5 g/cm.

Example 42

Comparative as Dispersion of MVTR-Modifying Material in Adhesive

Droplets of a 20% (w/w) aqueous solution of sodium carbonate monohydrate was added to the adhesive solution of Example 41 until approximately 20% of the acid groups present on the adhesive would be neutralized. The resulting adhesive mixture was slightly cloudy. Samples using this adhesive mixture were then prepared and tested as described in Example 41. The thickness of the adhesive was approximately 26 microns. The average upright MVTR and inverted MVTR values of four test specimens were 1360+/−20 g/m²/24 hours and 2030+/−60 g/m²/24 hours, respectively. The average adhesion to steel of five test specimens that were 2.54 cm wide was measured to be 140+/−3 g/cm.

TABLE 2

Summary of Experimental results for Examples 1-42

| Example | Adhesive | Backing | MVTR Modifying Composition | Upright (Dry) MVTR g/m²/24 hr +/− Std Dev | Inverted (Wet) MVTR g/m²/24 hr +/− Std Dev |
|---|---|---|---|---|---|
| 1 Comp. | 65/15/20 2-EHA/AA/ Pluronic 25R4 | PU film (58237 resin) | None | 1150 +/− 100 | 2340 +/− 190 |
| 2 Comp. | 65/15/20 2-EHA/AA/ Pluronic 25R4 | PU film (58237 resin) | Na-citrate | 1000 +/− 30 | 2350 +/− 90 |
| 3 Comp. | 65/15/20 2-EHA/AA/ Pluronic 25R4 | PU film (58237 resin) | Citric acid | 1180 +/− 60 | 1720 +/− 40 |
| 4 | 65/15/20 2-EHA/AA/ Pluronic 25R4 | PU film (58237 resin) | 0.15M NaOH | 1210 +/− 50 | 11400 +/− 1800 |
| 5 | 65/15/20 2-EHA/AA/ Pluronic 25R4 | PU film (58237 resin) | 0.3M NaOH | 1280 +/− 60 | 16900 +/− 740 |
| 6 | 65/15/20 2-EHA/AA/ Pluronic 25R4 | PU film (58237 resin) | Na-carbonate monohydrate | 1070 +/− 40 | 20800 +/− 980 |
| 7 | 65/15/20 2-EHA/AA/ Pluronic 25R4 | PU film (58237 resin) | Na-bicarbonate | 1340 +/− 100 | 19100 +/− 870 |
| 8 | 65/15/20 2-EHA/AA/ Pluronic 25R4 | PU film (58237 resin) | Potassium carbonate | 1390 +/− 40 | 20700 +/− 530 |
| 9 | 65/15/20 2-EHA/AA/ Pluronic 25R4 | PU film (58237 resin) | Potassium bicarbonate | 1650 +/− 20 | 20300 +/− 610 |
| 10 | 65/15/20 2-EHA/AA/ Pluronic 25R4 | PU film (58237 resin) | Na-carbonate monohydrate - with added untreated layers | 1190 +/− 100 | 16700 +/− 1700 |
| 11 | 65/15/20 2-EHA/AA/ Pluronic 25R4 | PU film (58237 resin) | Na-carbonate monohydrate - with added untreated layers between adhesive and treated layer | 1240 +/− 280 | 9150 +/− 1280 |
| 12 | 65/15/20 2-EHA/AA/ Pluronic 25R4 | PU film (58237 resin) | Layer 1 - Na-carbonate monohydrate Layer 2 - citric acid | 1080 +/− 30 | 9880 +/− 2660 |
| 13 | 65/15/20 2-EHA/AA/ Pluronic 25R4 | PU film (58237 resin) | Na-carbonate monohydrate on foam | 900 +/− 60 | 7840 +/− 1600 |
| 14 | 70/15/15 (IOA/AA/EOA + less than 1% PEOX) | PU film (58237 resin) | Na-carbonate monohydrate | 1660 +/− 60 | 18800 +/− 860 |
| 15 Comp. | 70/15/15 (IOA/AA/EOA + less than 1% PEOX) | PU film (58237 resin) | None | 1150 +/− 30 | 2520 +/− 250 |
| 16 Comp. | 50 micron thick 70/15/15 (IOA/AA/EOA + less than 1% PEOX) | PU film (58237 resin) | None | 690 +/− 40 | 1170 +/− 210 |
| 17 | 50 micron thick 70/15/15 (IOA/AA/EOA + less than 1% PEOX) | PU film (58237 resin) | Na-carbonate monohydrate | 1235 +/− 100 | 20700 +/− 500 |
| 18 | 70/15/15 (IOA/AA/EOA + | PU film (58237 | 3 layers - Na-carbonate | 1200 +/− 60 | 16000 +/− 2800 |

TABLE 2-continued

Summary of Experimental results for Examples 1-42

| Example | Adhesive | Backing | MVTR Modifying Composition | Upright (Dry) MVTR g/m$^2$/24 hr +/− Std Dev | Inverted (Wet) MVTR g/m$^2$/24 hr +/− Std Dev |
|---|---|---|---|---|---|
| | less than 1% PEOX) | resin) | monohydrate treated non-woven + absorbent non-woven + foam | | |
| 19 | 70/15/15 (IOA/AA/EOA + less than 1% PEOX) | PU film (58237 resin) | Same as example 22 except MVTR test solution was buffered | 1080 +/− 130 | 11200 +/− 1200 |
| 20 Comp. | 90/10 (IOA/AA) | PU film (58237 resin) | none | 820 +/− 10 | 1180 +/− 20 |
| 21 | 90/10 (IOA/AA) | PU film (58237 resin) | Na-carbonate monohydrate | 900 +/− 30 | 1440 +/− 50 |
| 22 Comp. | 25/69/6 (2-EHA/BA/AA) | PU film (58237 resin) | none | 1500 +/− 30 | 2400 +/− 160 |
| 23 | 25/69/6 (2-EHA/BA/AA) | PU film (58237 resin) | Na-carbonate monohydrate | 1570 +/− 80 | 2540 +/− 60 |
| 24 Comp. | 90/10 (IOA/AA) | SX-473 (Rayon/PET non-woven) | none | 1390 +/− 420 | Not tested |
| 25 | 90/10 (IOA/AA) | SX-473 (Rayon/PET non-woven) | Na-bicarbonate | 1860 +/− 260 | Not tested |
| 26 Comp. | 25/69/6 (2-EHA/BA/AA) | SX-473 (Rayon/PET non-woven) | none | 1380 +/− 150 | Not tested |
| 27 | 25/69/6 (2-EHA/BA/AA) | SX-473 (Rayon/PET non-woven) | Na-bicarbonate | 1680 +/− 250 | Not tested |
| 28 Comp. | 70/15/15 (IOA/AA/EOA + less than 1% PEOX) | PU film (58237 resin) | Sprayed droplets of water | 940 +/− 30 | 1600 +/− 490 |
| 29 | 70/15/15 (IOA/AA/EOA + less than 1% PEOX) | PU film (58237 resin) | Droplets of Na-carbonate monohydrate | 1530 +/− 30 | 9460 +/− 490 |
| 30 Comp. | 90/10 (IOA/AA) | PU film (58237 resin) | None | 640 +/− 15 | 1090 +/− 30 |
| 31 Comp. | 90/10 (IOA/AA) | PU film (58237 resin) | none | 820 +/− 15 | 1180 +/− 20 |
| 32 | 90/10 (IOA/AA) | PU film (58237 resin) | Na-carbonate monohydrate | 900 +/− 30 | 1440 +/− 50 |
| 33 Comp. | 25/69/6 (2-EHA/BA/AA) | PU film (58237 resin) | none | 1500 +/− 30 | 2400 +/− 160 |
| 34 | 25/69/6 (2-EHA/BA/AA) | PU film (58237 resin) | Na-carbonate monohydrate | 1570 +/− 80 | 2540 +/− 60 |
| 35 Comp. | 90/10 (IOA/AA) | PU film (58237 resin) | none | 920 +/− 10 | 1460 +/− 140 |
| 36 | 90/10 (IOA/AA) | PU film (58237 resin) | Na-carbonate monohydrate | 1040 +/− 60 | 1570 +/− 100 |
| 37 Comp. | 46.5/46/7.5 2-EHA/BA/AA | PU film (58237 resin) | none | 1560 +/− 30 | 2470 +/− 110 |

TABLE 2-continued

Summary of Experimental results for Examples 1-42

| Example | Adhesive | Backing | MVTR Modifying Composition | Upright (Dry) MVTR g/m²/24 hr +/− Std Dev | Inverted (Wet) MVTR g/m²/24 hr +/− Std Dev |
|---|---|---|---|---|---|
| 38 | 46.5/46/7.5 2-EHA/BA/AA | PU film (58237 resin) | Na-carbonate monohydrate | 1590 +/− 10 | 2590 +/− 130 |
| 39 Comp. | Amine adhesive 90/4/9 (2-EHA/ Acryamide/ DMAEMA) | PU film (58237 resin) | none | 950 +/− 40 | 1520 +/− 210 |
| 40 Comp. | Amine adhesive 90/4/9 (2-EHA/ Acryamide/ DMAEMA) | PU film (58237 resin) | Na-carbonate monohydrate | 990 +/− 30 | 1590 +/− 300 |
| 41 Comp. | 33% solids in ethyl acetate of 70/15/15 (IOA/AA/EOA + less than 1% PEOX) | PU film (58237 resin) | none | 1300 +/− 30 | 1950 +/− 110 |
| 42 Comp. | 33% solids in ethyl acetate of 70/15/15 (IOA/AA/EOA + less than 1% PEOX) | PU film (58237 resin) | Na-carbonate monohydrate to neutralize 20% acid groups in adhesive | 1300 +/− 30 | 1950 +/− 110 |

2-EHA = 2-ethylhexylacrylate
AA = Acrylic Acid
BA = butyl acrylate
EOA = methoxy poly(ethylene oxide) acrylate macromer
IOA = iso-octylacrylate
Na = sodium
PEOX = poly(ethyloxazoline)
Pluronic 25R4 = poly(ethylene polypropylene) copolymer diol from BASF, Mount Olive, NJ
PU = polyurethane Example 43

Comparative

An approximately 25 micron thick 85/15 (w/w) IOA/AA adhesive was pressure laminated to an approximately 25 micron thick polyurethane Estane 58237 film on a paper carrier. A 40 g/m² 70/30 (w/w) TENCEL/Polyester spunlaced non-woven (Ahlstrom Green Bay, Green Bay, Wis.) was then laminated by hand to the adhesive side of the adhesive/film laminate and the paper carrier was removed from the film side of the sample. Samples were tested seven days after lamination of the non-woven to the adhesive. The average upright MVTR and inverted MVTR values of four test specimens were 600+/−40 g/m²/24 hours and 750+/−30 g/m²/24 hours, respectively.

Example 44

The non-woven from Example 43 was saturated with a 4.0% (w/w) aqueous solution of sodium carbonate monohydrate at a rate of 13 feet/min (3.96 meter/min) and dried in a pilot scale forced air oven at approximately 105° C. for about 5 minutes. The coating weight of sodium carbonate monohydrate on the non-woven was 16.3 g/m². This coated non-woven was then laminated by hand to the adhesive side of the adhesive/film laminate from Example 43C. The specimens were tested seven days after lamination. The average upright MVTR and inverted MVTR values of four test specimens were 720+/−100 g/m²/24 hours and 1090+/−230 g/m²/24 hours, respectively.

Example 45

Comparative

An approximately 25 micron thick 87.5/12.5 (w/w) IOA/AA adhesive was pressure laminated to an approximately 25 micron thick polyurethane Estane 58237 film on a paper carrier. The untreated non-woven from Example 44 was then laminated by hand to the adhesive side of the adhesive/film laminate and the paper carrier was removed from the film side of the sample. Samples were tested seven days after lamination of the non-woven to the adhesive. The average upright MVTR and inverted MVTR values of four test specimens were 600+/−10 g/m²/24 hours and 800+/−20 g/m²/24 hours, respectively.

Example 46

This example was prepared and tested like Example 45 except the sodium carbonate coated non-woven from Example 44 was laminated by hand to the 87.5/12.5 (w/w) IOA/AA adhesive side of the adhesive/film laminate, instead of an untreated non-woven. The average upright MVTR and inverted MVTR values of four test specimens were 600+/−20 g/m²/24 hours and 910+/−100 g/m²/24 hours, respectively.

Example 47

Comparative

An approximately 25 micron thick 80/10/10 (w/w/w) IOA/AA/EOA adhesive was pressure laminated to an approximately 25 micron thick polyurethane Estane 58237 film on a paper carrier. The untreated non-woven from Example 44 was then laminated by hand to the adhesive side of the adhesive/film laminate and the paper carrier was removed from the film side of the sample. Samples were tested seven days after lamination of the non-woven to the adhesive. The average upright MVTR and inverted MVTR values of four test specimens were 1580+/−40 g/m$^2$/24 hours and 3070+/−130 g/m$^2$/24 hours, respectively.

Example 48

This example was prepared and tested like Example 47 except the sodium carbonate coated non-woven from Example 44 was laminated by hand to the 80/10/10 (w/w/w) IOA/AA/EOA adhesive side of the adhesive/film laminate, instead of an untreated non-woven. The average upright MVTR and inverted MVTR values of four test specimens were 1440+/−110 g/m$^2$/24 hours and 3350+/−190 g/m$^2$/24 hours, respectively.

Example 49

Comparative

An approximately 25 micron thick 75/12.5/12.5 (w/w/w) IOA/AA/EOA adhesive was pressure laminated to an approximately 25 micron thick polyurethane Estane 58237 film on a paper carrier. The untreated non-woven from Example 44 was then laminated by hand to the adhesive side of the adhesive/film laminate and the paper carrier was removed from the film side of the sample. Samples were tested seven days after lamination of the non-woven to the adhesive. The average upright MVTR and inverted MVTR values of four test specimens were 1500+/−100 g/m$^2$/24 hours and 2870+/−240 g/m$^2$/24 hours, respectively.

Example 50

This example was prepared and tested like Example 49 except the sodium carbonate coated non-woven from Example 44 was laminated by hand to the 75/12.5/12.5 (w/w/w) IOA/AA/EOA adhesive side of the adhesive/film laminate, instead of an untreated non-woven. The average upright MVTR and inverted MVTR values of four test specimens were 1450+/−80 g/m$^2$/24 hours and 11400+/−600 g/m$^2$/24 hours, respectively.

Example 51

Comparative

An approximately 25 micron thick 84/6/10 (w/w/w) IOA/AA/EOA adhesive was pressure laminated to an approximately 25 micron thick polyurethane Estane 58237 film on a paper carrier. The untreated non-woven from Example 44 was then laminated by hand to the adhesive side of the adhesive/film laminate and the paper carrier was removed from the film side of the sample. Samples were tested seven days after lamination of the non-woven to the adhesive. The average upright MVTR and inverted MVTR values of four test specimens were 1880+/−90 g/m$^2$/24 hours and 4250+/−260 g/m$^2$/24 hours, respectively.

Example 52

This example was prepared and tested like Example 51 except the sodium carbonate coated non-woven from Example 44 was laminated by hand to the 84/6/10 (w/w/w) IOA/AA/EOA adhesive side of the adhesive/film laminate, instead of an untreated non-woven. The average upright MVTR and inverted MVTR values of four test specimens were 1740+/−40 g/m$^2$/24 hours and 5400+/−1400 g/m$^2$/24 hours, respectively.

Example 53

Comparative

An approximately 25 micron thick 74/6/20 (w/w/w) IOA/AA/EOA adhesive was pressure laminated to an approximately 25 micron thick polyurethane Estane 58237 film on a paper carrier. The untreated non-woven from Example 44 was then laminated by hand to the adhesive side of the adhesive/film laminate and the paper carrier was removed from the film side of the sample. Samples were tested seven days after lamination of the non-woven to the adhesive. The average upright MVTR and inverted MVTR values of four test specimens were 2410+/−80 g/m$^2$/24 hours and 8350+/−510 g/m$^2$/24 hours, respectively.

Example 54

This example was prepared and tested like Example 53 except the sodium carbonate coated non-woven from Example 44 was laminated by hand to the 74/6/20 (w/w/w) IOA/AA/EOA adhesive side of the adhesive/film laminate, instead of an untreated non-woven. The average upright MVTR and inverted MVTR values of four test specimens were 2190+/−50 g/m$^2$/24 hours and 10500+/−1780 g/m$^2$/24 hours, respectively.

TABLE 3

Summary of Experimental results for Examples 43-54

| Example | Adhesive | Backing | MVTR Modifying Composition | Upright (Dry) MVTR g/m$^2$/24 hr +/− Std Dev | Inverted (Wet) MVTR g/m$^2$/24 hr +/− Std Dev |
|---|---|---|---|---|---|
| 43 Comp. | 85/15 IOA/AA | HP film (58237 resin) | None | 600 +/− 40 | 750 +/− 30 |

TABLE 3-continued

Summary of Experimental results for Examples 43-54

| Example | Adhesive | Backing | MVTR Modifying Composition | Upright (Dry) MVTR g/m²/24 hr +/− Std Dev | Inverted (Wet) MVTR g/m²/24 hr +/− Std Dev |
|---|---|---|---|---|---|
| 44 | 85/15 IOA/AA | HP film (58237 resin) | Na-carbonate monohydrate | 720 +/− 100 | 1090 +/− 230 |
| 45 Comp. | 87.5/12.5 IOA/AA | HP film (58237 resin) | none | 600 +/− 10 | 800 +/− 20 |
| 46 | 87.5/12.5 IOA/AA | HP film (58237 resin) | Na-carbonate monohydrate | 600 +/− 20 | 910 +/− 100 |
| 47 Comp. | 80/10/10 IOA/AA/EOA | HP film (58237 resin) | none | 1580 +/− 40 | 3070 +/− 130 |
| 48 | 80/10/10 IOA/AA/EOA | HP film (58237 resin) | Na-carbonate monohydrate | 1440 +/− 110 | 3350 +/− 190 |
| 49 Comp. | 75/12.5/12.5 IOA/AA/EOA | HP film (58237 resin) | none | 1500 +/− 100 | 2870 +/− 240 |
| 50 | 75/12.5/12.5 IOA/AA/EOA | HP film (58237 resin) | Na-carbonate monohydrate | 1450 +/− 80 | 11400 +/− 600 |
| 51 Comp. | 84/6/10 IOA/AA/EOA | HP film (58237 resin) | none | 1880 +/− 90 | 4250 +/− 260 |
| 52 | 84/6/10 IOA/AA/EOA | HP film (58237 resin) | Na-carbonate monohydrate | 1740 +/− 40 | 5400 +/− 1400 |
| 53 Comp. | 74/6/20 IOA/AA/EOA | HP film (58237 resin) | none | 2410 +/− 80 | 8350 +/− 510 |
| 54 | 74/6/20 IOA/AA/EOA | HP film (58237 resin) | Na-carbonate monohydrate | 2190 +/− 50 | 10500 +/− 1780 |

AA = Acrylic Acid
IOA = iso-octylacrylate
EOA = methoxy poly(ethylene oxide) acrylate macromer The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A medical article comprising:
  a PSA layer comprising acid-functional groups or basic-functional groups, wherein the PSA includes at least 0.84 mmoles acidic- or basic-functional groups per gram PSA; and
  an MVTR-modifying material that is basic when the PSA comprises acidic-functional groups or is acidic when the PSA comprises basic-functional groups; wherein the MVTR-modifying material is immiscible with the PSA, and reacts with the functional groups of the PSA upon contact to form a poly-salt in the presence of fluid;
  wherein the MVTR-modifying material is incorporated within a scaffold that is in contact with the PSA layer.

2. The medical article of claim 1, wherein the PSA comprises a functional polymer, and wherein said polymer is prepared from at least 6 wt-% acidic- or basic-functional monomers, based on the total weight of the PSA.

3. The medical article of claim 1, wherein the PSA includes at least 1.8 mmoles acidic- or basic-functional groups per gram PSA.

4. The medical article of claim 1, wherein the PSA includes no greater than 4.2 mmoles acidic- or basic-functional groups per gram PSA.

5. The medical article of claim 1, further comprising a second PSA layer, wherein the MVTR-modifying material is disposed between the two PSA layers.

6. The medical article of claim 1, wherein the molar ratio of the MVTR-modifying material to the functional groups is 0.1:1 to 100:1.

7. The medical article of claim 1, wherein the PSA comprises basic-functional groups, and the MVTR-modifying material is acidic.

8. The medical article of claim 7, wherein the PSA comprises an amine polymer.

9. The medical article of claim 1, wherein the MVTR-modifying material improves the wet MVTR of the medical article by at least 20% relative to the same medical article without the MVTR-modifying material.

10. A medical article comprising:
  a PSA layer comprising acid-functional groups or basic-functional groups, wherein the PSA includes at least 0.84 mmoles acidic- or basic-functional groups per gram PSA;

an MVTR-modifying material that is basic when the PSA comprises acidic-functional groups or is acidic when the PSA comprises basic-functional groups; wherein the MVTR-modifying material is immiscible with the PSA, and reacts with the functional groups of the PSA upon contact to form a poly-salt in the presence of fluid; and a pH-altering layer, wherein the MVTR-modifying material is disposed between the PSA layer and the pH-altering layer, and wherein the pH-altering layer comprises a pH-altering material.

11. A medical article comprising:
a PSA layer comprising acid-functional groups or basic-functional groups, wherein the PSA includes at least 0.84 mmoles acidic- or basic-functional groups per gram PSA;
an MVTR-modifying material that is basic when the PSA comprises acidic-functional groups or is acidic when the PSA comprises basic-functional groups; wherein the MVTR-modifying material is immiscible with the PSA, and reacts with the functional groups of the PSA upon contact to form a poly-salt in the presence of fluid; and
a filtration layer, wherein the filtration layer is disposed between the MVTR-modifying material and a target site.

12. The medical article of claim 11, wherein the MVTR-modifying material is disposed on a surface of the PSA layer.

13. The medical article of claim 12, wherein the MVTR-modifying material is pattern coated onto the surface of the PSA layer.

14. A medical article comprising:
a PSA layer comprising acid-functional groups or basic-functional groups, wherein the PSA includes at least 0.84 mmoles acidic- or basic-functional groups per gram PSA;
an MVTR-modifying material that is basic when the PSA comprises acidic-functional groups or is acidic when the PSA comprises basic-functional groups; wherein the MVTR-modifying material is immiscible with the PSA, and reacts with the functional groups of the PSA upon contact to form a poly-salt in the presence of fluid;
a carrier film in contact with the PSA layer;
an absorbent pad disposed between the carrier film and the adhesive layer; and
a backing disposed between a support layer and the PSA layer, wherein the medical article is a wound dressing.

15. A medical article comprising:
a PSA layer comprising a polymer having acid-functional groups, wherein the PSA includes at least 0.84 mmoles acidic-functional groups per gram PSA; and
a basic MVTR-modifying material;
wherein the MVTR-modifying material is immiscible with the PSA, and reacts with the functional groups of the PSA upon contact to form a poly-salt in the presence of fluid; and
wherein the MVTR-modifying material comprises a base selected from a group consisting of sodium hydroxide, potassium hydroxide, calcium hydroxide, lithium hydroxide, silver hydroxide, zinc hydroxide, ammonium hydroxide, magnesium hydroxide, barium hydroxide, strontium hydroxide, cesium hydroxide, rubidium hydroxide, ammonium carbonate, sodium carbonate, sodium bicarbonate, potassium carbonate, potassium bicarbonate, silver carbonate, lithium carbonate, lithium bicarbonate, barium bicarbonate, magnesium carbonate, cesium carbonate, hydrates thereof, and combinations thereof.

16. The medical article of claim 15, wherein the PSA comprises rubber based adhesives, (meth)acrylics, poly(alpha-olefin)s, polyurethane, silicones, and combinations thereof.

17. A wound dressing comprising:
a backing having a first major surface and a second major surface;
a PSA layer disposed on at least a portion of the first major surface of the backing; wherein the PSA comprises acid-functional groups or basic-functional groups, wherein the PSA includes at least 0.84 mmoles acidic- or basic-functional groups per gram PSA; and
an MVTR-modifying layer proximate the PSA layer; wherein the MVTR-modifying layer comprises a scaffold;
wherein the MVTR-modifying layer comprises an MVTR-modifying material that is basic when the PSA comprises acidic-functional groups, or is acidic when the PSA comprises basic-functional groups; and
wherein the MVTR-modifying material is immiscible with the PSA, and reacts with the functional groups to form a poly-salt upon contact in the presence of fluid.

18. The wound dressing of claim 17, wherein the PSA comprises basic amine groups.

19. A wound dressing comprising:
a backing having a first major surface and a second major surface;
a PSA layer disposed on at least a portion of the first major surface of the backing;
wherein the PSA comprises acid-functional groups or basic-functional groups, wherein the PSA includes at least 0.84 mmoles acidic- or basic-functional groups per gram PSA;
an absorbent layer, wherein the absorbent layer comprises a polymeric fabric, a polymeric foam, or a combination thereof; and
an MVTR-modifying layer proximate the PSA layer; wherein the MVTR-modifying layer comprises an MVTR-modifying material that is basic when the PSA comprises acidic-functional groups, or is acidic when the PSA comprises basic-functional groups;
wherein the MVTR-modifying material is immiscible with the PSA, and reacts with the functional groups to form a poly-salt upon contact in the presence of fluid.

20. The wound dressing of claim 19, wherein the MVTR-modifying layer is in direct contact with at least a portion of the PSA layer.

21. The wound dressing of claim 19, wherein the PSA comprises carboxylic acid groups.

22. The wound dressing of claim 21 wherein the MVTR-modifying material comprises a base selected from a group consisting of sodium hydroxide, potassium hydroxide, calcium hydroxide, lithium hydroxide, silver hydroxide, zinc hydroxide, ammonium hydroxide, magnesium hydroxide, barium hydroxide, strontium hydroxide, cesium hydroxide, rubidium hydroxide, ammonium carbonate, sodium carbonate, sodium bicarbonate, potassium carbonate, potassium bicarbonate, silver carbonate, lithium carbonate, lithium bicarbonate, barium bicarbonate, magnesium carbonate, cesium carbonate, hydrates thereof, and combinations thereof.

23. A wound dressing comprising:
a backing having a first major surface and a second major surface;
a PSA layer disposed on at least a portion of the first major surface of the backing; wherein the PSA layer comprises acid-functional groups;

a support layer releasably adhered to the second major surface of the backing; and an MVTR-modifying layer comprising an MVTR-modifying material in contact with the PSA layer, wherein the PSA layer does not include MVTR-modifying material uniformly dispersed throughout;

wherein the MVTR-modifying material is basic, is immiscible with the PSA, and reacts with the functional groups to form a poly-salt upon contact in the presence of fluid.

24. The wound dressing of claim 23, wherein the PSA includes at least 0.84 mmoles acidic-functional groups per gram PSA.

25. The wound dressing of claim 23, wherein the polymer is prepared from at least 6 wt-% acidic-functional monomers, based on the total weight of the PSA.

26. A method of increasing the moisture vapor transmission rate of an adhesive layer in a medical article, the method comprising:

providing a PSA layer comprising acid-functional groups or basic-functional groups, wherein the PSA includes at least 0.84 mmoles acidic- or basic-functional groups per gram PSA;

providing an MVTR-modifying material that is basic when the PSA comprises acidic-functional groups or is acidic when the PSA comprises basic-functional groups, wherein the MVTR-modifying material is immiscible with the PSA; and placing the MVTR-modifying material in the medical article at a location that allows the MVTR-modifying material to contact the PSA when the medical article comes in contact with fluid during use;

wherein contact between the MVTR-modifying material, the PSA, and fluid causes an acid-base reaction to form a poly-salt and increase the moisture permeability of at least a portion of the PSA layer.

27. The method of claim 26, wherein the polymer is prepared from at least 6 wt-% acidic- or basic-functional monomers, based on the total weight of the PSA.

28. The method of claim 26, wherein placing the MVTR-modifying material in the medical article at a location that allows the MVTR-modifying material to contact the PSA includes coating the MVTR-modifying material onto the PSA layer.

29. The method of any one of claims 26 through 28 placing the MVTR-modifying material in the medical article at a location that allows the MVTR-modifying material to contact the PSA includes:

providing a scaffold;

coating the scaffold with the MVTR-modifying material; and contacting at least a portion of the PSA layer with the coated scaffold.

* * * * *

UNITED STATES PATENT AND TRADEMARK OFFICE
CERTIFICATE OF CORRECTION

PATENT NO.        : 8,546,637 B2
APPLICATION NO.   : 12/942489
DATED             : October 1, 2013
INVENTOR(S)       : David Holm et al.

It is certified that error appears in the above-identified patent and that said Letters Patent is hereby corrected as shown below:

In the Specification

Column 3
Line 12              Delete "backing" and insert -- backing. --, therefor.
Line 14              Delete "backing" and insert -- backing. --, therefor.

Column 10
Line 63              Delete "backing)" and insert -- backing). --, therefor.

Column 14
Line 34              Delete "backing" and insert -- backing. --, therefor.

Column 17
Line 60              Delete "backings" and insert -- backings. --, therefor.

Column 18
Lines 53-54          Delete "Rheinhold," and insert -- Reinhold, --, therefor.

Column 25
Line 9               Delete "polypropylene" and insert -- poly(propylene --, therefor.

Column 26
Line 2               Delete "Lycocell-Rayon/Polyester" and insert -- Lyocell-Rayon/Polyester --, therefor.
Line 19 (Approx.)    Delete "Lycocell-Rayon/Polyester" and insert -- Lyocell-Rayon/Polyester --, therefor.

Column 38
Line 11 (Approx.)    Delete "dimethyaminoethly" and insert -- dimethylaminoethyl --, therefor.

Signed and Sealed this
Fourth Day of November, 2014

Michelle K. Lee
*Deputy Director of the United States Patent and Trademark Office*

Columns 43-44 (Table 2)
Line 12 (Approx.)		Delete "Acryamide/" and insert -- Acrylamide/ --, therefor.
Line 17 (Approx.)		Delete "Acryamide/" and insert -- Acrylamide/ --, therefor.